United States Patent [19]

Iwata et al.

[11] Patent Number: 5,293,538
[45] Date of Patent: Mar. 8, 1994

[54] METHOD AND APPARATUS FOR THE INSPECTION OF DEFECTS

[75] Inventors: Hisafumi Iwata; Yukio Matsuyama, both of Yokohama; Hitoshi Kubota, Hujisawa, all of Japan

[73] Assignee: Hitachi, Ltd., Tokyo, Japan

[21] Appl. No.: 705,537

[22] Filed: May 24, 1991

[30] Foreign Application Priority Data

May 25, 1990 [JP] Japan .................................. 2-133792

[51] Int. Cl.$^5$ .................................................. G01N 21/47
[52] U.S. Cl. ...................................... 356/237; 356/239
[58] Field of Search .................... 356/237, 239, 430; 250/201.6

[56] References Cited

U.S. PATENT DOCUMENTS

| | | | |
|---|---|---|---|
| 3,814,946 | 6/1974 | Takahashi et al. | 356/430 |
| 4,469,442 | 9/1984 | Reich | 356/364 |
| 4,669,875 | 6/1987 | Shiba et al. | 356/237 |
| 4,671,663 | 6/1987 | Sick | 356/430 |
| 4,674,875 | 6/1987 | Koizumi | 356/237 |
| 4,740,079 | 4/1988 | Koizumi et al. | 356/237 |
| 4,886,975 | 12/1989 | Murakami et al. | 356/430 |
| 5,162,642 | 11/1992 | Akamatsu et al. | 250/201.6 |

Primary Examiner—Richard A. Rosenberger
Attorney, Agent, or Firm—Antonelli, Terry, Stout & Kraus

[57] ABSTRACT

A defect inspection method and apparatus detect a defect which exists on the surface of a protection layer or a defect which exists in the protection layer and scatters the light on its surface, through the detection of the light which is derived from an illumination light and reflected on the protection layer surface and the light which is derived from a slit-formed illumination light and scattered in the area between the position where the light is incident to the transparent protection layer and the position where the surface of an element underneath the transparent protection layer is illuminated. An image process, which images two elements having the same appearance and compares the images, thereby to reduce inconsistent components emerging in portions other than a defective portion, is conducted through imaging under the bright field illumination and bright-/dark field combined illumination, and the images are rendered the minimum filtering process based on 3-by-3 pixels and the defect judgement process based on comparison.

6 Claims, 24 Drawing Sheets

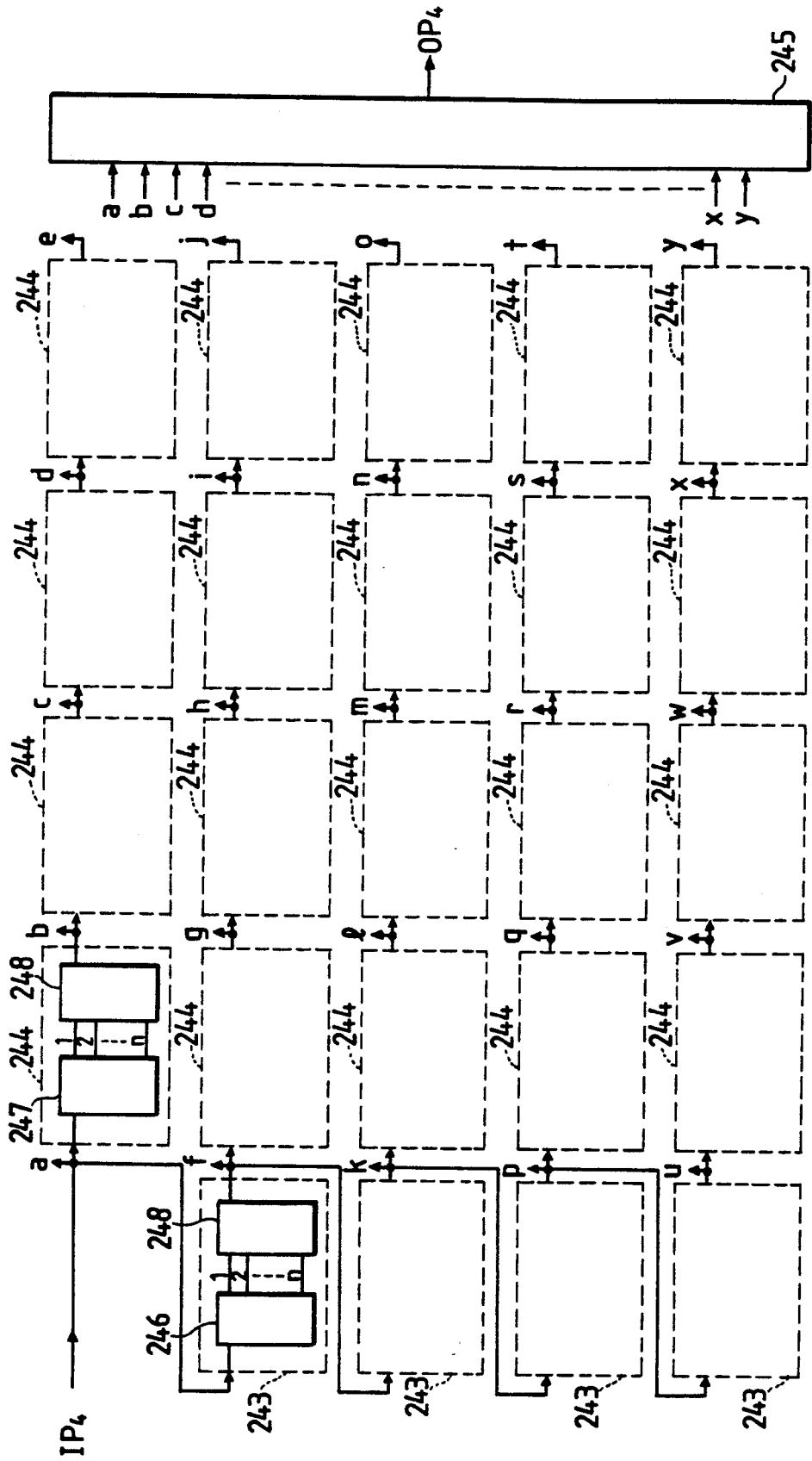

FIG. 16a
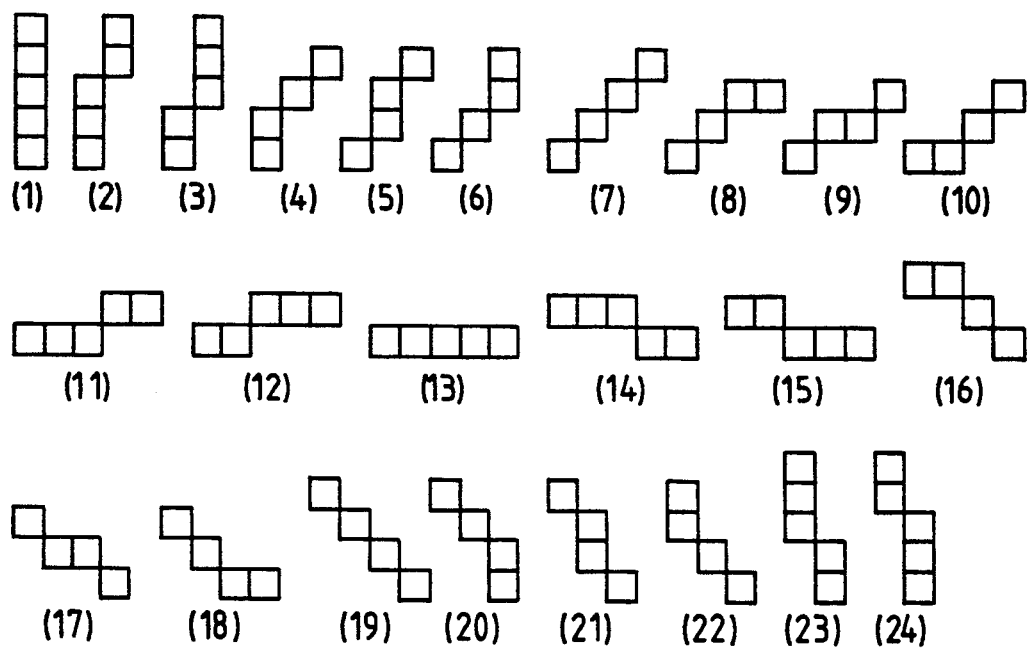
FIG. 16b
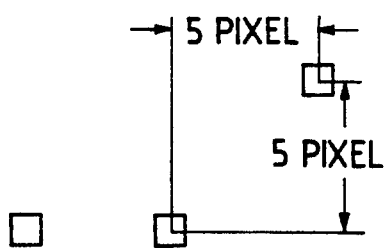

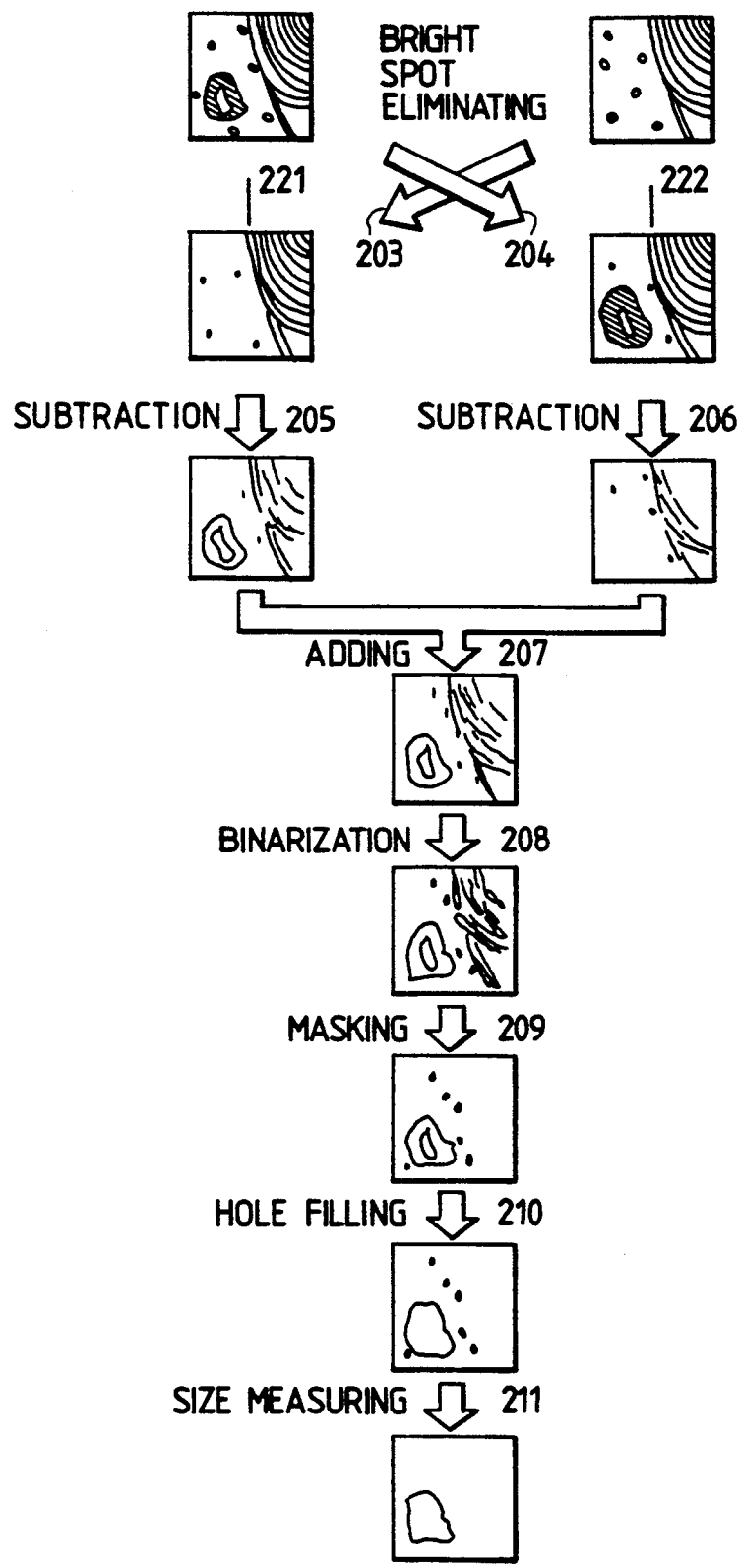

METHOD AND APPARATUS FOR THE INSPECTION OF DEFECTS

BACKGROUND OF THE INVENTION

The present invention relates to a method and apparatus for the inspection of visual defects on an object under test. The object may be an element coated with a transparent protection layer, such as a thin-film magnetic head used in a magnetic disk unit of a large computer system.

Pertinent conventional techniques applicable to a thin-film magnetic head will be explained. A thin-film magnetic head is fabricated by forming a number of elements on a ceramic wafer (termed simply "wafer" hereinafter) and thereafter separating the wafer into pieces. FIG. 1a is a plan view of an element, and FIG. 1b is a cross-sectional view taken along the line A—A' of FIG. 1a. The element is formed on a wafer 5, and is made up of a coil 1, a magnetic member 2, an insulation layer 4, and a transparent protection layer 3 which covers the components.

The protection layer may contain defects as shown in FIG. 2. A foreign particle 6 is a fragment of impurity which has fallen into and is embedded in the protection layer during the formation of the protection layer for example, and it may be a transparent particle which scatters the light on its surface or an opaque particle which virtually does not reflect the light. A void 8 is a recess which is formed after a foreign particle embedded in the protection layer has been ejected during the polishing process, and an etching remnant 9 is a part of a metallic pattern which has been left unremoved in the etching process.

If metal or other substance on the protection layer of the thin-film magnetic head falls to the disk surface during the operation of the magnetic disk unit, such a serious event as data loss will result due to head crashing. If a foreign particle or metallic etching remnant included in the protection layer appears on the side of a die following die separation, it will cause a crack or erosion by moisture on the protection layer, resulting in a pronounced degradation of reliability of the element. On this account, the protection layer must be inspected for defects thoroughly. However, these defects cannot be detected in terms of the electrical or magnetic characteristics of the element, and therefore visual inspection is indispensable.

A conventional technique for detecting a defect or foreign particle on an electronic circuit pattern is based on the bright field illumination (the light is incident perpendicularly to the object) or dark field illumination (the light is incident obliquely to the object), and the comparison of images of two inspection objects that have intrinsically the same appearance thereby to detect an inconsistent portion as a defect of one object. For example, supposing the presence of an etching remnant 9 on the surface of the protection layer of the coil 1, as shown in FIG. 3a and FIG. 3b which is a cross-sectional view taken along the line C—C' of FIG. 3a, the coil 1 has a rough surface which scatters the light, and therefore the etching remnant 9 is detected as a bright image and the background coil 1 is detected as a dark image under the bright field illumination. Conversely, the etching remnant is detected as a dark image on the bright background under the dark field illumination. In any case, the defect has a high contrast image (the difference of brightness between the defect and its background), and the etching remnant 9 can be detected on the basis of comparison as an inconsistency between images of two elements that should have the same appearance inherently.

An example of conventional techniques for the visual inspection of thin-film magnetic heads is described in the proceeding of "The 4th Symposium on the Industrial Image Sensing Technique", items 106 through 111, sponsored by The Japanese Society for Non-Destructive Inspection, published in 1989, in which the area of pattern of the magnetic member is measured under the bright field illumination, and a defective shape of the magnetic member 2 is detected through the comparison of the measured area with the reference value.

The conventional technique based on the comparison of images of two elements having the same appearance is greatly affected by the element surface characteristics (roughness of the surface) coated by the protection layer. For example, supposing the presence of a transparent foreign particle 6 which reflects the light on its surface on the coil 1, as shown in FIG. 4a and FIG. 4b, which is a cross-sectional view taken along the line d—d' of FIG. 4a, with the coil 1 and foreign particle 6 have the nature of light scattering on the surface. Accordingly, both of the transparent foreign particle 6 and coil 1 are detected as dark images under the bright field illumination, or they are detected as bright images under the dark field illumination. As a result, the transparent foreign particle 6 has a low contrast in the whole image, and its detection will be difficult due to a small difference of element images in the comparative inspection. Another example of difficult defect detection is the presence of an etching remnant 9 on the magnetic member 2, as shown in FIG. 5a and FIG. 5b, which is a cross-sectional view taken along the line B—B' of FIG. 5a. Both the magnetic member 2 and etching remnant 9 have a smooth surface, and they are detected as bright images under the bright field illumination or as dark images under dark field illumination, providing a low contrast defect.

The conventional technique based on the measurement of a pattern area and the comparison of it with the reference value also relies on the premise that the defective portion has a high contrast. Therefore, the technique will not be applicable to low-contrast defects, as mentioned above.

As described above, the conventional techniques do not consider various cases of the material of element and defect in the transparent protection layer and their surface property and optical characteristics, as encountered in the inspection of thin-film magnetic heads. On this account, if a defect which exists in the protection layer resembles the background element surface in the optical characteristics, the defect produces a low-contrast image, making its detection difficult.

SUMMARY OF THE INVENTION

The present invention resides in the method and apparatus for the visual inspection of such an element coated with a transparent protection layer as a thin-film magnetic head. The method and apparatus are capable of detecting accurately a defect on the surface of the transparent protection layer. The method and apparatus of the present invention are also capable of detecting a defect which exists in the protection layer and scatters the light without being affected by the reflected light from the element surface. The inventive method and apparatus are also capable of detecting reliably a low-contrast, opaque foreign particle which exists in the protection layer and virtually does not reflect the light based on the comparison of images of two elements having the same appearance. The inventive method and apparatus are also capable of high-accuracy inspection for a defect on the surface of or inside the transparent protection layer based on the automatic focusing operation.

Specifically, the present invention is intended to detect a defect which exists on the surface of a protection layer and a defect which exists in the protection layer and scatters the light on the surface of the defect, through the detection of the light which is the regular reflection on the protection layer surface and the light which scatters from the area between the position at which a slit-formed illumination light is incident to the transparent protection layer and the position reflection on the element surface beneath the transparent protection layer, and designed to image the element under the bright field illumination and the bright/dark field combined illumination for conducting the imaging process which reduces inconsistent components emerging outside of the defective portion during the comparison of images of two elements having the same appearance, implement the minimum filtering process based on 3-by-3 pixels for the images, and thereafter implement the comparative judgement process.

BRIEF DESCRIPTION OF THE DRAWINGS

FIG. 15 is a block diagram showing an example of the arrangement of the judgement process circuit used in the inventive bright field illumination, device-to-device comparision method;

FIGS. 16a and 16b are diagrams explaining the operators of the size measuring circuit;

FIG. 17 is a diagram explaining the image process based on the inventive bright field illumination, device-to-device comparision method;

DESCRIPTION OF THE PREFERRED EMBODIMENT

Figure 1A:
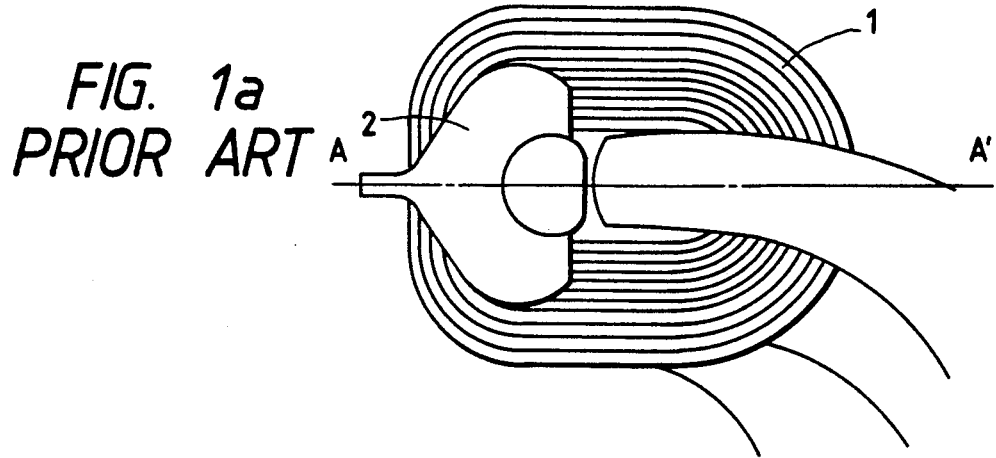
FIGS. 1a and 1b are diagrams showing the structure of a thin-film magnetic head as an object to be inspected.
Figure 1B:
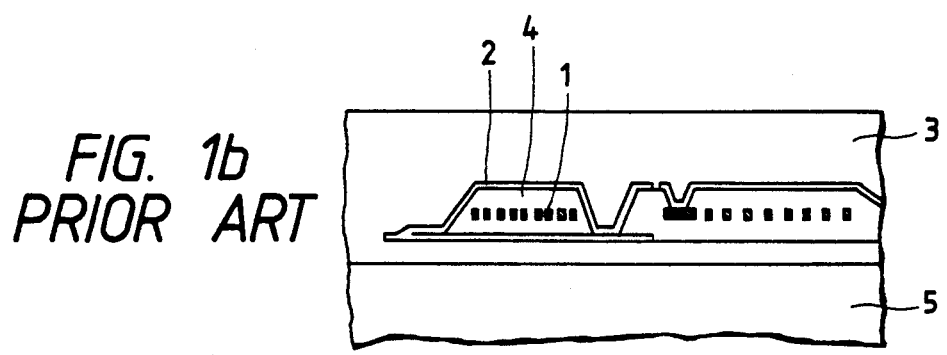
Figure 2:
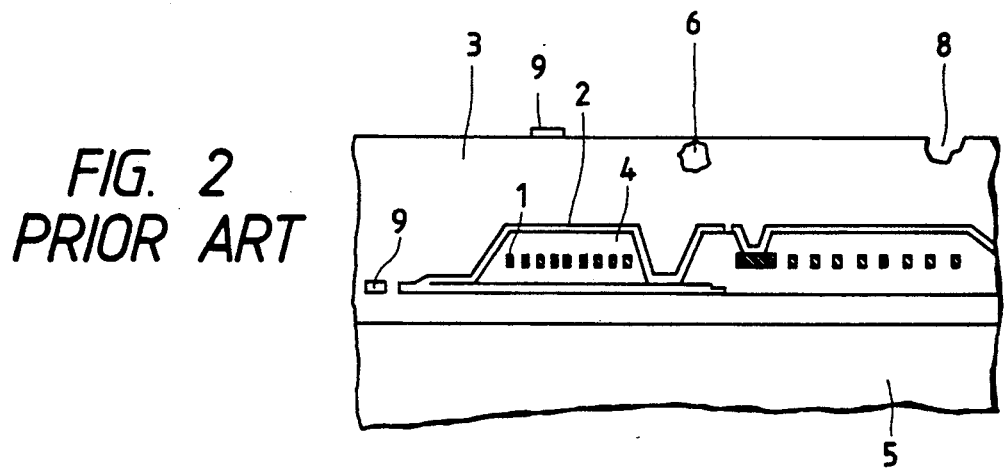
FIG. 2 is a diagram explaining defects to be detected.
Figure 3A:
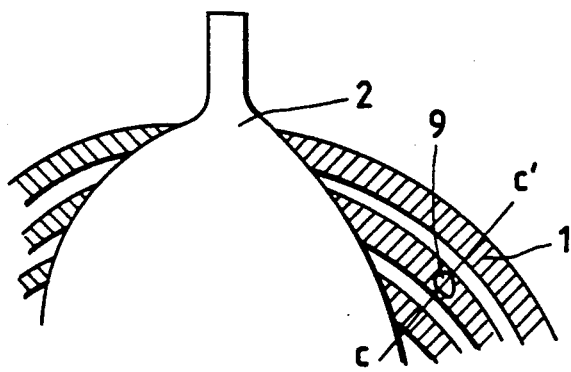
FIGS. 3a and 3b are diagrams showing an example of defects which can be detected by the conventional technique.
Figure 3B:
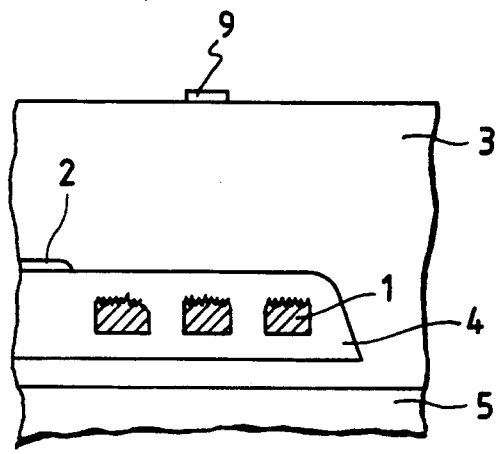
Figure 4A:
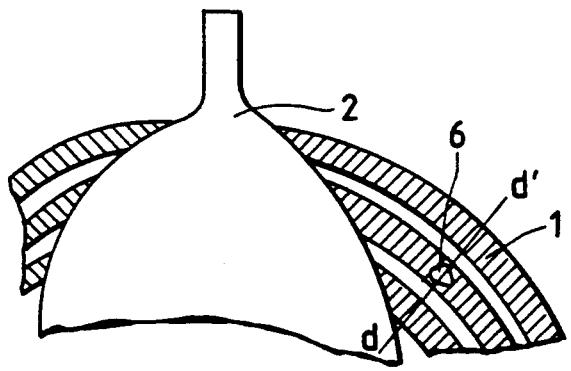
FIGS. 4a and 4b are diagrams showing an example of defects which cannot be detected by the conventional technique.
Figure 4B:
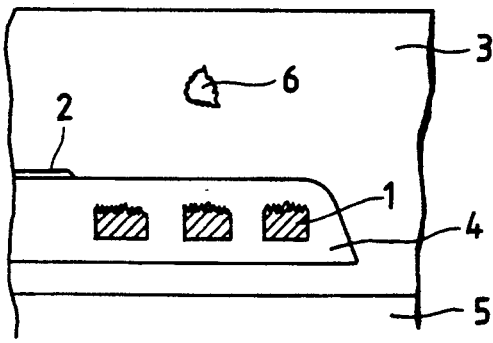
Figure 5A:
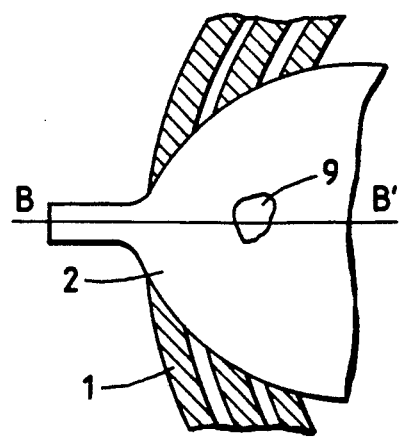
FIGS. 5a and 5b are diagrams showing another example of defects which cannot be detected by the conventional technique.
Figure 5B:
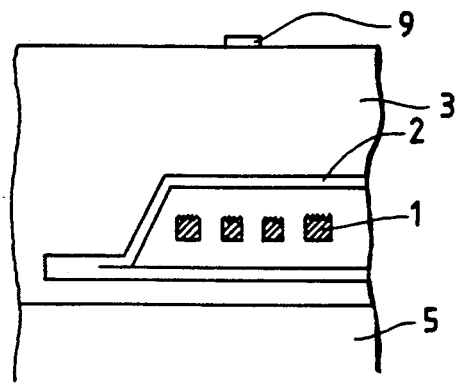

The objective of the present invention for detecting a defect on the surface of a protection layer is achieved through the projection of a slit-formed illumination light obliquely to an object under test, the detection of only the light which is the regular reflection of the illumination light on the surface of the protection layer, and the binarization of the detected signal.

The objective of the present invention for detecting a defect which exists in the protection layer and scatters the light on its surface is achieved through the projection of a slit illumination light obliquely to an object under test, the detection of the light which scatters from the area between the position at which the slit illumination light is incident to the transparent protection layer and the illuminated position of the object surface under the transparent protection layer, and the binarization of for the detected signal.

Accordingly, the objectives of the present invention for detecting a defect on the surface of the protection layer and a defect which exists in the protection layer and scatters the light on its surface are achieved through the projection of a slit illumination light obliquely to an object under test, and the detection of the light which is the regular reflection of the illumination light on the surface of the protection layer and the light which scatters from the area between the position at which the slit illumination light is incident to the transparent protection layer and the illuminated position of the object under the transparent protection layer.

In order for the conventional technique, which is based on the comparison of images of two elements having the same appearance, to accomplish the defect detection reliably, it necessary to utilize an image process for reducing inconsistent components emerging in portions other than the defective portion. The present invention deals with this matter by imaging the object through bright field illumination and bright/dark field combined illumination, implementing the minimum filtering process based on 3-by-3 pixels for the images, and thereafter implementing comparative judgement process.

The foregoing automatic focusing is accomplished by focusing the light, which is the regular reflection of the slit illumination light on the protection layer surface, on an image sensor, with its scanning direction being orthogonal to the slit light, and detecting the position of the slit light from the output signal waveform of the image sensor.

The intensity of the light, which is the regular reflection on the protection layer of the oblique incident illumination light, is correspondent to the reflectivity of the protection layer surface. Accordingly, when an etching remnant which is high in reflectivity exists at the light incident position, it is detected as a brighter image relative to the protection layer surface. A void which is a recess on the layer surface has no reflective surface and it is detected as a dark image.

When a transparent foreign particle exists on the light path of the illumination light, the light is scattered on its surface. By detecting the light which scatters from the area between the position at which the slit illumination light is incident to the transparent protection layer and the illuminated position of the element surface coated with the transparent protection layer, it is possible to detect only the scattered light from the foreign particle and it can be detected as a bright image. Accordingly, through the detection of the regular reflection light from the protection layer surface and the scattered light from the foreign particle, it is possible to detect defects existing on the surface of and inside the protection layer.

Through the implementation of the minimum filtering process based on 3-by-3 pixels for images produced under the bright field illumination and bright/dark field combined illumination, it is possible to remove bright spots (portions of brighter appearance having higher reflectivity than their periphery) existing on the baked ceramic wafer and bright spots emerging on such a rough pattern surface as the coil section caused by the dark field illumination component, thereby reducing inconsistent components between images in normal portions as compared with those of defective portions.

By focusing the light, which is the regular reflection of the slit illumination light on the protection layer, on the image sensor with its scanning direction being orthogonal to the slit light, it is possible to detect the vertical motion of the wafer as the position of the slit light included in the output signal waveform of the image sensor. Accordingly, automatic focusing is accomplished by moving the wafer mounting stage vertically so that the slit light is detected at a fixed position invariably.

Next, the method and apparatus for the visual inspection of a thin-film magnetic head based on embodiments of the present invention will be described with reference to the drawings.

Figure 6:
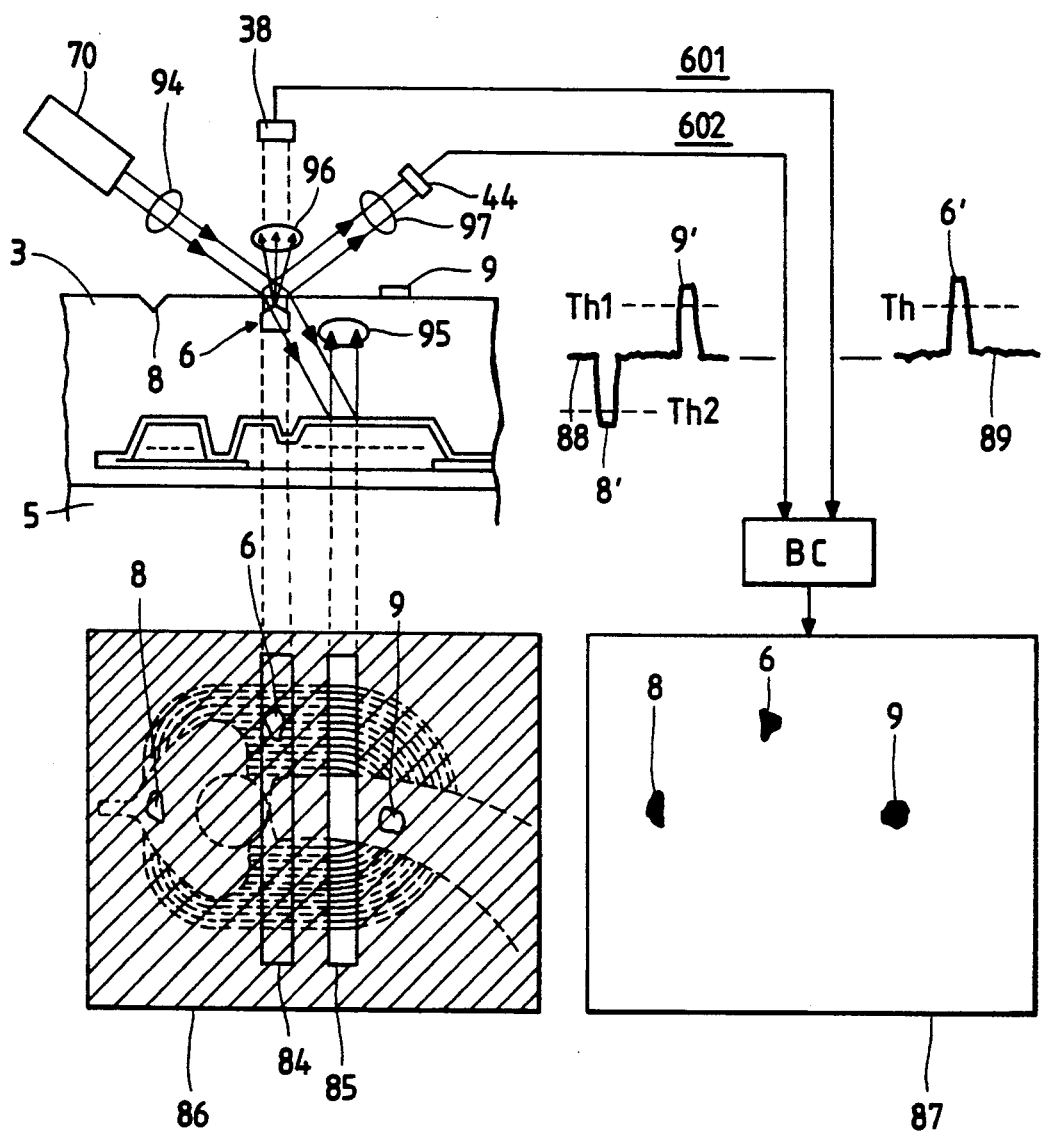
FIG. 6 is a diagram explaining the visual inspection method based on an embodiment of the present invention.

FIG. 6 is a diagram explaining the visual inspection method based on an embodiment of the present invention. The figure shows the detection of a transparent foreign particle 6 which exists in a protection layer and scatters the light on its surface, and the detection of a void 8 and an etching remnant 9 existing on the protection layer surface.

The former is based on the method which has been proposed by the inventors of the present invention in Japanese Patent Application No. 2-28546. In this method, a slit illumination light is projected obliquely to a wafer 5, as shown in FIG. 6. The illumination light beam 94 has its cross section elongated in the direction normal to the drawing, thereby to have a slit-formed shape. Part of the illumination light is refracted on the surface of a protection layer 3 and incident to the protection layer, and it reaches the element surface under the protection layer. Observation from above the wafer gives the appearance as shown by 86, in which only the element in an area 85 is bright by illumination. If a transparent foreign particle 6 exists on the illumination light path, the light is scattered on the particle surface. A linear sensor 38 having an alignment of pixels in parallel to the slit illumination light is placed above the wafer for detecting an area, e.g., area 84, between the incident position of the slit light 94 to the protection layer 3 and the illuminated area 85, and it detects only a scattered light 96 from the transparent foreign particle 6 without including the reflected light 95 from the element in the area 85. In this state, the linear sensor 38 produces a signal waveform 89 indicating that only the transparent foreign particle 6 is bright as shown by the waveform 6', and only the defect can be detected through the process with a binarization circuit BC having a proper threshold Th. This method will be called "scattered light detection method".

The latter is based on the detection of the light 97 which is the regular reflection of the slit light 94 on the surface of the protection layer 3 with a linear sensor 44 having an alignment of pixels parallel to the slit illumination light. In the absence of a defect on the protection layer surface, part of the slit illumination light is incident to the protection layer 3 and the rest is reflected regularly. If a metallic etching remnant 9 which is high in reflectivity exists on the protection layer surface, most of the illumination light is reflected by it, and due to an increased intensity of regular reflection it is detected as a brighter image than the case of absent defect. A void, 8 which is a recess on the protection layer surface, has no inherent reflection surface, and it is detected as a dark image. The signal waveform 88 shown in FIG. 6 is the case where the metallic etching remnant 9 (shown by the waveform 9') and the void 8 (shown by the waveform 8') are located inside the view field of the linear sensor 44. The etching remnant 9 is detected as a brighter image than the protection layer surface, while the void 8 is detected as a darker image than the protection layer surface. Accordingly, through a simple threshold process, it is possible to discriminate defects to be the etching remnant 9 for the waveform section above the threshold Th1 and to be the void 8 for the waveform section below the threshold Th2. This method will be called "reflected light detection method".

Figure 7:
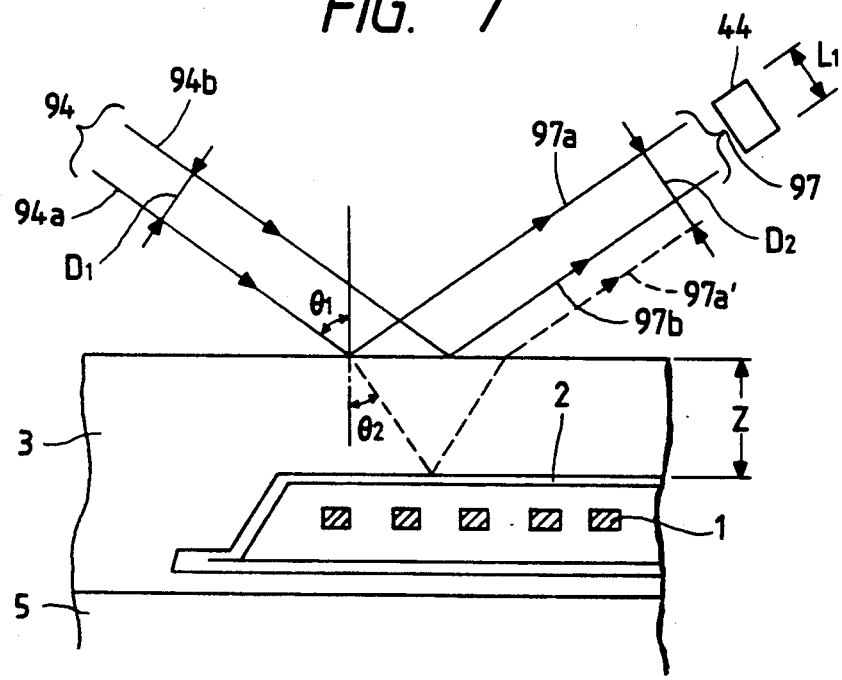
FIG. 7 is a diagram showing the optical system of the defect inspection method based on an embodiment of the present invention.

FIG. 7 shows in detail the position of illumination and the position of detection by the linear sensor 44 based on the reflected light detection method. In the figure, the slit illumination light has edges defined by 94a and 94b. An illumination light component 94a is partly reflected on the surface of protection layer 3 to produce a reflected light component 97a and partly incident to the protection layer and reflected on the element surface to produce a reflected light component 97a'. In order to detect only the light component reflected on the protection layer, the linear sensor 44 needs to be sensitive only to the reflected light at the edge defined by 97a and 97a'. Namely, for the width $L_1$ of detection of the linear sensor 44 and the width $D_2$ of light beam between 97a and 97a' on the protection layer surface, the following condition must be met.

$$L_1 < D_2 (=2 \cdot Z \cdot \tan(\arcsin(N_1 \sin\theta_1/N_2)) \cdot \cos\theta_1) \tag{1}$$

where $\theta_1$ is the incident angle of the illumination light, $\theta_2$ is the refraction angle of the light in the protection layer, Z is the thickness of the protection layer over the element, $N_1$ the refractivity of air, and $N_2$ is the refractivity of the protection layer.

In the reflected light detection method, through the setting of the thickness of protection layer over the element, the incident angle of illumination light and the detection width of linear sensor in compliance with the above condition, it is possible to detect only the reflected light from the protection layer surface without being affected by the reflected light from the element surface. By projecting a slit illumination light obliquely to the wafer 5 and detecting the scattered light from the inside of protection layer with the linear sensor 38, a transparent foreign particle 6 in the protection layer can be detected, and by detecting the reflected light from the surface of protection layer with the linear sensor 44, an etching remnant 9 and void 8 on the protection layer surface can be detected, as mentioned previously. By merely implementing a proper threshold process, these defects can surely be detected as shown by 87 in FIG. 6.

However, defects in the transparent protection layer also include transparent foreign particles which do not reflect the light on the surface, and the above-mentioned scattered light detection method which is based on the detection of the scattered light from foreign particles cannot detect these defects. The following describes a method of inspection intended for transparent foreign particles which do not reflect the light.

Figure 8:
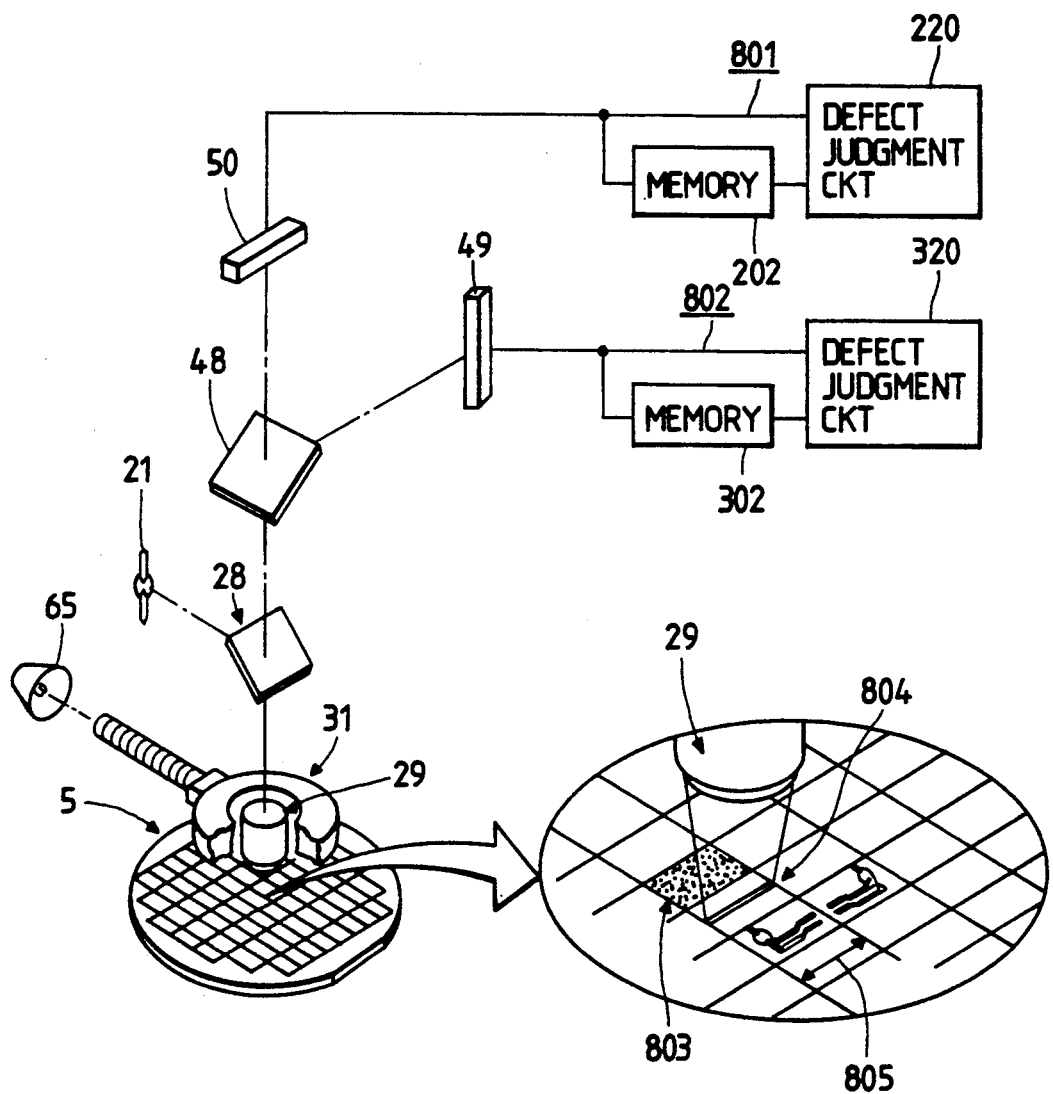
FIG. 8 is a diagram explaining the visual inspection method based on another embodiment of the present invention.

FIG. 8 is a diagram used to explain the visual inspection method, which is intended for transparent foreign particles, based on an embodiment of the present invention. This inspection method covers the detection of transparent foreign particles in the protection layer in the area where no element is formed (a portion of the wafer where the ceramic base is seen through the protection layer when observed from above the water this portion; will be called "unpatterned area"), and the detection of opaque foreign particles in the protection layer over an element, and etching remnants in the protection layer in the unpatterned area.

The former will be called "bright field illumination, device-to-device comparision method", and the latter will be called "bright/dark field combined illumination, device-to-device comparision method". The bright-/dark field combined illumination stands for the simultaneous implementation of the bright field illumination and the dark field illumination. Each of the methods bases the operation n the sequential imaging of multiple elements formed the wafer and comparing images of two adjoining elements, thereby to detect a different portion as a defect.

Figure 9:
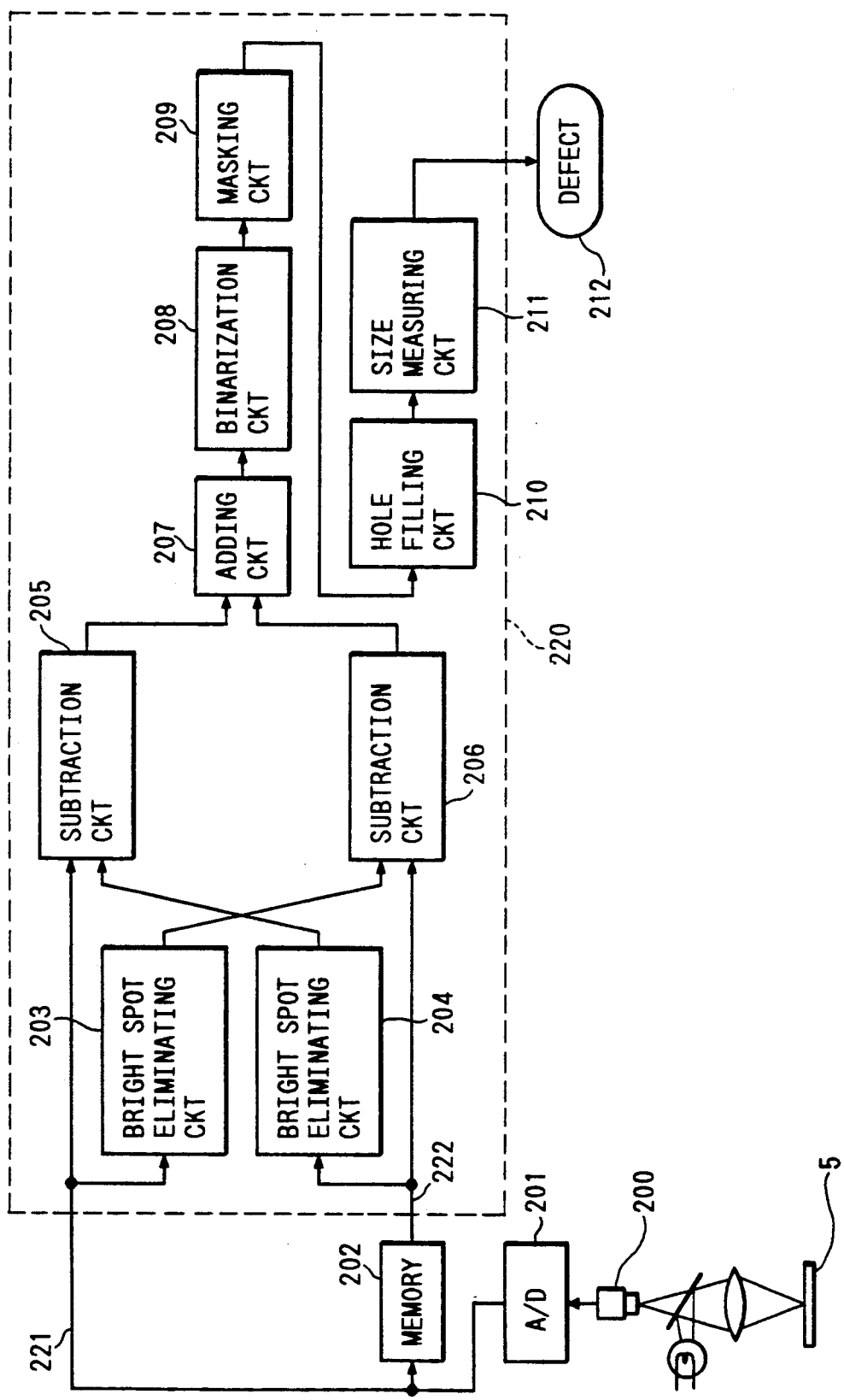
FIG. 9 is a block diagram showing the bright field illumination, device-to-device comparison method based on an embodiment of the present invention.

First, the bright field illumination, device-to-device comparision method will be explained with reference to FIG. 9 showing the method based on an embodiment of this invention. Bright field illumination is conducted for a wafer 5, and resultant reflected light is collected for imaging by an image sensor 200. The output of the image sensor 200 is converted into digital image data by an A/D converter 201, and image data of one element is stored as a reference image in a memory 202. Subsequently, an adjacent element is imaged by the image sensor 200, and at the same time the reference image data is read out of the memory 202. The immediate test image data 221 is compared with the reference image data 222 by an image processing circuit 220, thereby to detect a defect.

Bright spot elimination circuits 203 and 204 are used to remove bright spots existing on the baked ceramic wafer so as to facilitate the detection of low-contrast foreign particles in unpatterned areas. The bright spot elimination is accomplished by slicing a partial image of 3-by-3 pixels out of the input image and delivering the minimum value of brightness among the nine pixels as a value of the central pixel (minimum filtering process).

Each of subtraction circuits 205 and 206 evaluates in absolute value the difference of brightness between the two input images when one input image is darker than the other, or produces a "0" output (indicative of the absence of defect) when the one input image is brighter than the other. Consequently, these circuits in combination detect a dark defect included in the one image and a bright defect included in the other image. A summing circuit 207 sums the outputs of the subtraction circuits 205 and 206, gathering all dark defects and bright defects included in the test image data 221 and reference image data 222.

The output of the summing circuit 207 is converted into binarization data at a proper threshold by a binarization circuit 208, and thereafter the data is processed to have "0" values (absence of defect) for areas other than the test area, i.e., unpatterned area, by a masking circuit 209, and the result is delivered to a hole filling circuit 210. The hole filling unit 210 has a role of filling the hole of a ring-shaped defect image so that a fear-stage size measuring circuit 211 does not malfunction. The size measuring circuit 211 extracts defects larger than the prescribed size as true defects from among the input defect image data.

The following explains the details of the arrangement and operation of each circuit.

Figure 10:
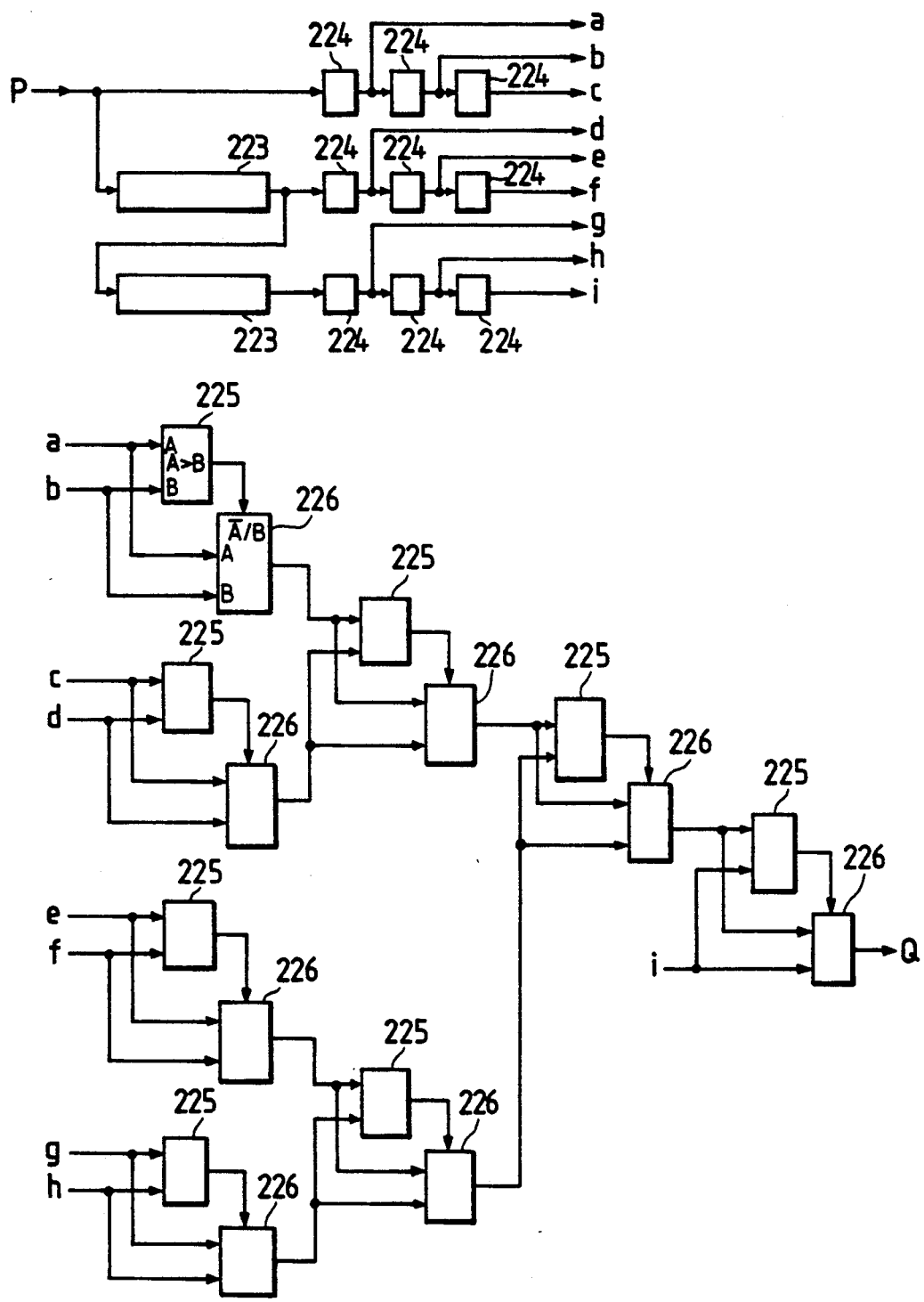
FIG. 10 is a block diagram showing an example of the arrangement of the bright spot elimination circuit used in the inventive bright field illumination, device-to-device comparision method.

FIG. 10 shows, as an example, the arrangement of the bright spot elimination circuit 203. The input image data is fed through a line memory 223 and latch circuit 224 so that a partial image of 3-by-3 pixels is sliced, and the minimum value among the nine pixels is extracted by means of comparators 225 and selectors 226. By choosing the image sensor to have such a range of detection that most of bright spots on the ceramic wafer are detected in size smaller than 2-by-2 pixels, these bright spots can mostly be removed from the image data.

Figure 11:
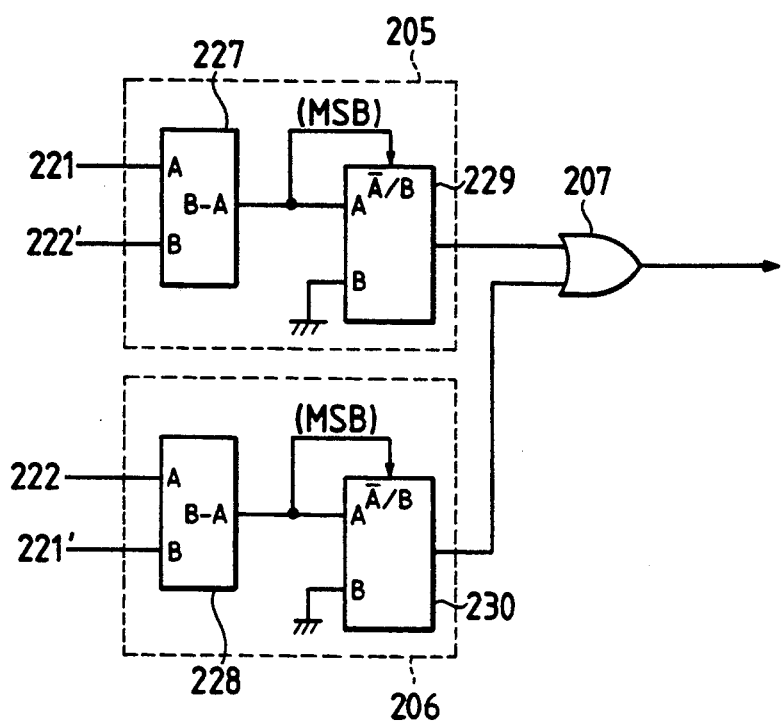
FIG. 11 is a block diagram of an example of the subtraction circuit.

FIG. 11 shows, as an example, the arrangement of the subtraction circuits 205 and 206 and the summing circuit 207. The subtraction circuit 205 receives the test image data 221 on its one input and image data resulting from bright spot elimination for the reference image data 222 on its other input 222'. The subtraction circuit 206 receives the reference image data 222 on its one input and image data resulting from bright spot elimination for the test image data 221 on its other input 221'. Both circuits extract portions of crude image data darker than the counterparts that have been rendered bright spot elimination. Specifically, the circuit is configured so that a selector 229 (or 230) connected to the output of the subtraction circuit 227 (or 228) selects its input for delivery if the subtraction circuit produces a positive output as a result of subtraction of the one image data from the other image data, or delivers a "0" output if the subtraction circuit produces a negative output. since it is logically impossible for the selectors 229 and 230 to produce non-zero outputs simultaneously, the summing circuit 207 can be a simple logical OR gate provided for each bit of data. The foregoing sequential operations of bright spot elimination, subtraction and summation can be expressed as follows.

$$D(i,j) = D1(i,j) + D2(i,j) \qquad (2)$$

(i) For $\min_{m,n}\{R(i+m, j+n)\} > T(i,j)$:

$$D1(i,j) = \min_{m,n}\{R(i+m, j+n)\} - T(i,j) \qquad (3)$$

(ii) Otherwise:
$$D1(i,j) = 0 \qquad (4)$$

(iii) For $\min_{m,n}\{T(i+m, j+n)\} > R(i,j)$:

$$D2(i,j) = \min_{m,n}\{T(i+m, j+n)\} - R(i,j) \qquad (5)$$

(iv) Otherwise:
$$D2(i,j) = 0 \qquad (6)$$

In the above cases (i) through (iv), parameters m and n take any of −1, 0 and 1. The terms R(i,j) and T(i,j) represent the brightness of pixels at coordinates (i,j) of the reference image 222 and test image 221, respectively. The term D(i,j) is the output image data of the summing circuit 207, and the terms D1(i,j) and D2(i,j) are output image data of the subtraction circuits 205 and 206, respectively.

Figure 12:
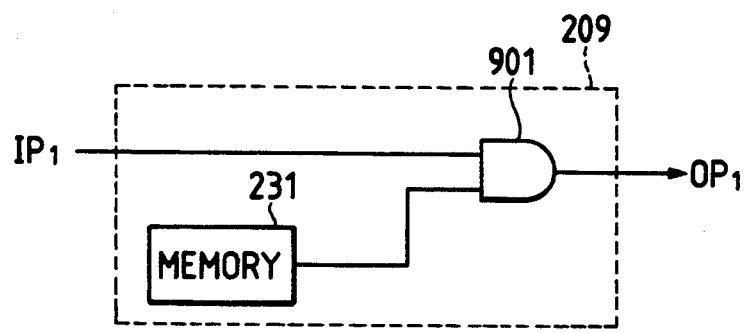
FIG. 12 is a block diagram of an example of the masking circuit.

FIG. 12 shows, as an example, the arrangement of the masking circuit 209. A memory 231 stores image data, with the test area (unpatterned area) being filled with "1" and remaining areas being filled with "0", and the data is read out in synchronism with the entry of image data. Through the logical AND operation for the input image data and the counterpart read out of the memory, areas other than the test area are all reduced to "0" (absence of defect).

Figure 13:
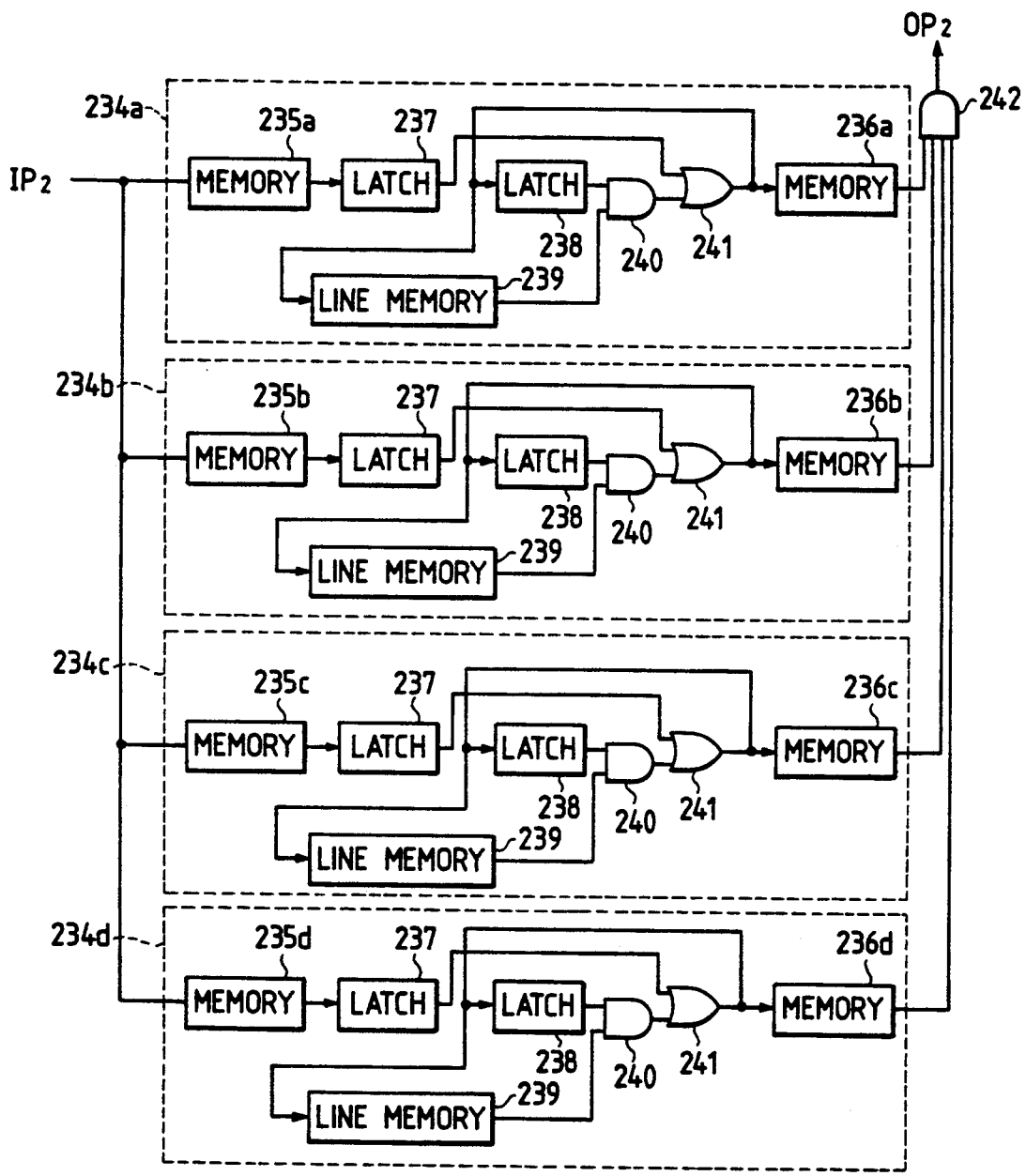
FIG. 13 is a block diagram of an example of the hole filling circuit.

FIG. 13 shows, as an example, the arrangement of the hole filling circuit 210. The operation of the circuit will be explained with reference to FIG. 14. In FIG. 13, indicated by 235a-235d and 236a-236d are memories, each storing 1-pixel data. Circuit sections 234a-234d have the same arrangement, but they are different in memory address control for writing.

First, the operation of the circuit 234a will be explained. The input image data is stored temporarily intact in the memory 235a. Image data is read out sequentially and held in a latch circuit 237. A logical OR gate 241 has processed image data on its output, and another latch circuit 238 holds the value of the previously processed pixel. A line memory 239 holds the values of the pixels which have been processed for the previous line. Accordingly, each circuit section implements a recursive process which produces "1" if the input pixel value (output of latch 237) is "1" or if the previous pixel value and the pixel value of the previous line are both "1". As a result of this process, the input image is varied as shown by (a) in FIG. 14. The processed image data is stored in the memory 236a.

The circuit 234b of FIG. 13 differs from 234a only in that the X address of the memories 235b and 236b are down-counted at writing. These memories are up-counted for the Y address at writing and the X and Y addresses at reading as usual. The memories of the circuit 234c are down-counted for the Y address at writing, and those of the circuit 234d are down-counted for the X and Y addresses at writing. The address control for the memories in this manner is equivalent to changing of the starting point of recursive process of the circuits 234a-234d as shown by the arrows in FIG. 14.

Figure 14:
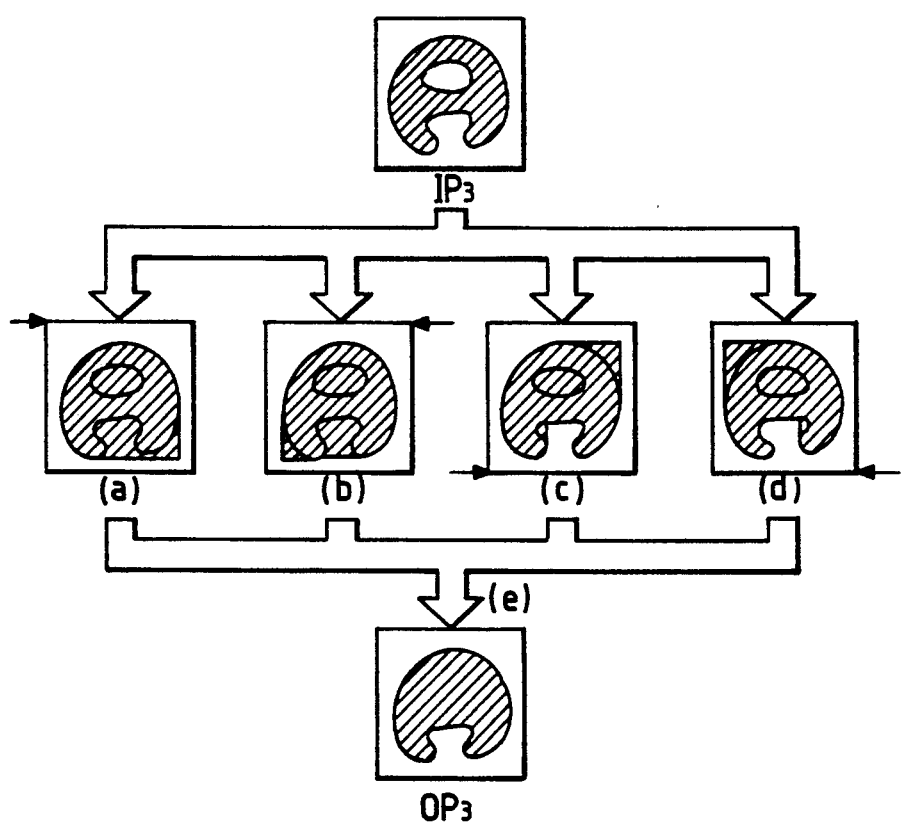
FIG. 14 is a diagram explaining the operation of the hole filling circuit.

In consequence, the processed images shown by (a)–(d) in FIG. 14 are stored in the memories 236a-236d. The contents of the memories are read out and rendered the logical AND operation thereby to accomplish the hole filling process.

The recursive processes implemented by the circuits 234a-234d are expressed as follows.

(i) Circuit 234a:

$$O1(i,j) = I(i,j) \cup O1(i-1,j) \cap O1(i,j-1) \qquad (7)$$

(ii) Circuit 234b:

$$O2(i,j) = I(i,j) \cup O2(i+1,j) \cap O2(i,j-1) \qquad (8)$$

(iii) Circuit 234c:

$$O3(i,j) = I(i,j) \cup O3(i-1,j) \cap O3(i,j+1) \qquad (9)$$

(iv) Circuit 234d:

$$O4(i,j) = I(i,j) \cup O4(i+1,j) \cap O4(i,j+1) \qquad (10)$$

where I is the input image data, and O1-O4 are processed image data stored in the memories 236a-236d. The symbols ∪ and ∩ stand for the logical OR and logical AND operations, respectively.

FIG. 15 shows, as an example, the arrangement of the size measuring circuit 211. The circuit discriminates a defect to be greater than a prescribed value if at least one of reference operators shown as examples in FIGS. 16a and 16b is included geometrically in the defective portion of the input image. For the image sensor having a detection range of 2.5 μm for example, the reference operators of FIG. 16a can detect defects greater than 10 μm. However, it is difficult for the circuit design to deal with a larger threshold value by increasing the number of pixels of operator in proportion. Therefore, the present invention is designed to use enlarged basic operators, with some pixels being extracted, thereby to deal with an increased value of threshold. FIG. 16b shows an example of such operators used to discriminate a defect with a 5-fold scale, i.e., 50 μm, for example.

In FIG. 15, indicated by 246 is a line memory, which produces delayed outputs of line 1 through line n simultaneously. 247 is a shift register, which produces delayed outputs of pixel 1 through pixel n simultaneously.

Each set of n delayed outputs from the line memory 246 and shift register 247 is entered to a selector 248, which selects a delayed signal in response to the specified threshold value of discrimination. A logical operation circuit 245 implements proper logical operations for outputs of selectors so as to make functions of operators shown in FIGS. 16a and 16b. For the convenience of modification of operators, the logical operation circuit 245 may be configured with a programmable integrated circuit device. By manipulating the outputs of selectors 248, an arbitrary number of pixels can be extracted for each operator.

The operation of each circuit will further be explained with reference to an example of image processing shown in FIG. 17. A test image 221 includes a foreign particle in the unpatterned area, whereas a reference image 222 includes no defect. The test image and reference image are rendered by the bright spot elimination process as shown by 203 and 204, and thereafter the individual subtraction operations as shown by 205 and 206. Included in each resultant image are the defect to be detected, some bright spots which have not been removed completely, and a small part of inconsistent components (due to a positioning error at imaging). Both images are summed as shown by 207, and binarized as shown by 208, and then the element pattern section is masked as shown by 209. Consequently, the inconsistent components of the element pattern are removed. Finally, a hole in the image of defect is filled by the hole filling circuit as shown by 210, and the size of the defect is discriminated for the defect judgement as shown by 211.

As described above, the inventive bright field illumination, device-to-device comparision method is capable of detecting stably low-contrast foreign particles existing in the unpatterned area without being affected by bright spots emerging on the ceramic wafer.

Next, the bright/dark field combined illumination, device-to-device comparision method will be explained.

Figure 18:
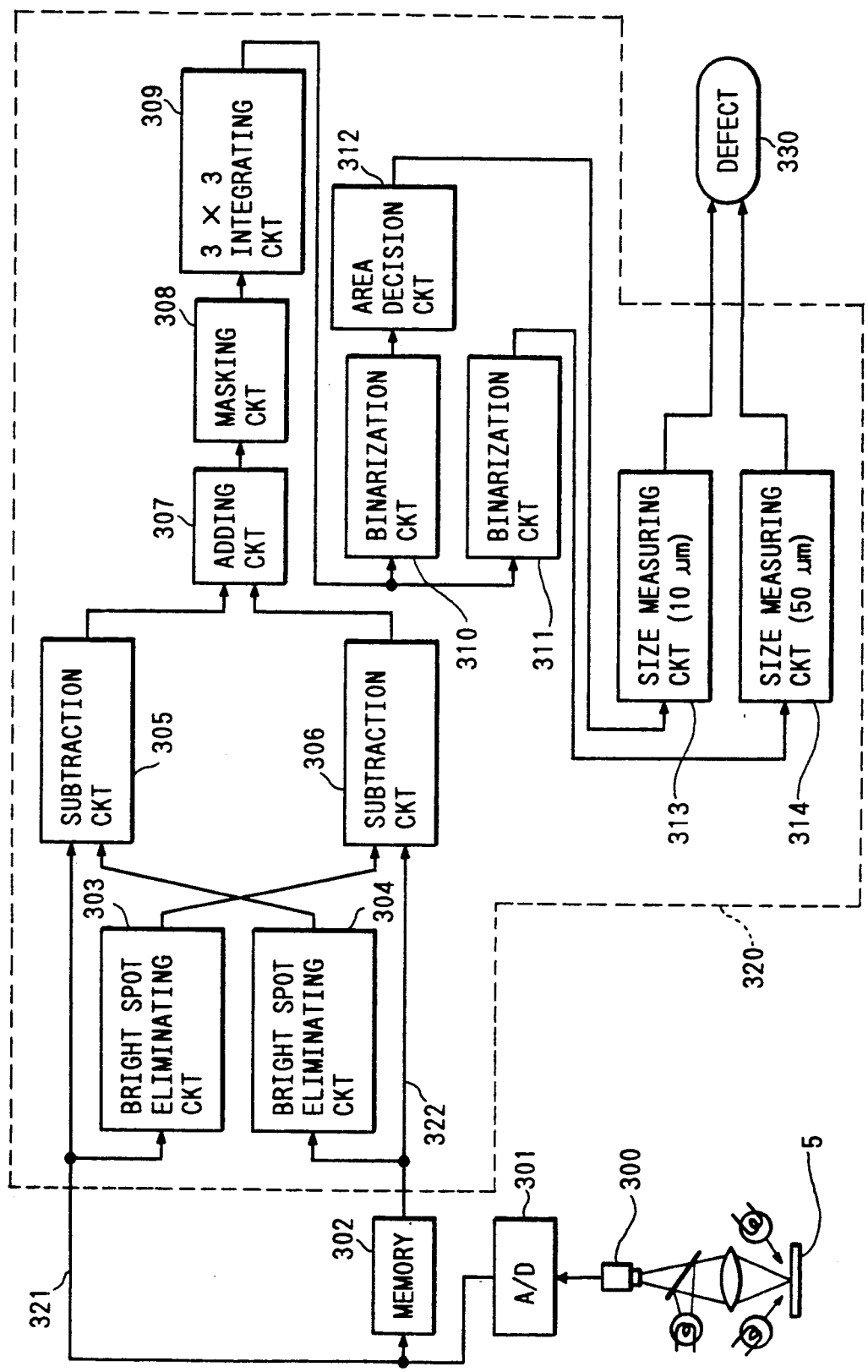
FIG. 18 is a block diagram showing an embodiment of the arrangement for carrying out the inventive bright field illumination, device-to-device comparision method.

FIG. 18 shows, as an embodiment, the arrangement of the apparatus based on this method. The method is intended for the detection of opaque foreign particles existing in the protection layer and etching remnants in the protection layer over the unpatterned area. Bright the field illumination and dark field illumination are applied simultaneously to a wafer 5, and the reflected light is collected for imaging with an image sensor 300. Since both of a smooth surface portion and rough surface portion are detected as bright images under the bright/dark field combined illumination, an opaque foreign particle in the protection layer over an element and an etching remnant in the protection layer in the unpatterned area are detected as high-contrast images.

The output of the image sensor 300 is converted into digital image data by an A/D converter 301, and image data of one element is stored as reference image data in a memory 302. Subsequently, an adjacent element is imaged by the image sensor 300, and at the same time the reference image data is read out of the memory 302. The immediate test image data 321 is compared with the reference image data 322 by an image processing circuit 320 shown in FIG. 18, thereby to detect a defect.

Bright spot elimination circuits 303 and 304, subtraction circuits 305 and 306, and summing circuit 307 are all identical to those in the previous embodiment of the bright field illumination, device-to-device comparision method. Bright spot elimination under the bright field illumination is intended to remove bright spots on the wafer, whereas in this embodiment it is intended to remove bright spots created by the dark field illumination in a rough surface pattern section. The dark field illumination causes a slant pattern section to be detected as a bright image. On this account, if two elements to be compared are different even slightly in the slant angle of pattern, the comparison of these portions (OutPut of the summing circuit 307) will result in a significant inconsistency. In order to avoid improper judgement of defect in this situation for favorably acceptable portions, such slant pattern sections are masked off to "0" (absence of defect). Remaining inconsistent components are further reduced through the averaging process for the image data by a 3-by-3 pixels integration circuit 309 and thereafter result is converted into binarization data.

This embodiment is further provided with an area discrimination circuit 312 with the intention of setting different defect judgement thresholds depending on the area under test (e.g., a defect of 10 $\mu$m or larger is detected in the protection layer over a element, and a defect of 50 $\mu$m or larger is detected in the unpatterned area). The area discrimination circuit 312 has a record of areas to which thresholds of judgement set in the rear-stage size measuring circuit 313 are applied. In this embodiment, the output of the 3-by-3 pixel integration circuit 309 is converted into binarization data at different thresholds by the binarization circuits 310 and 311, and their resultant data are entered to size measuring circuits 313 and 314 with a 10 $\mu$m and 50 $\mu$m thresholds, respectively, through the area discrimination circuit 312. This arrangement enables the inspection at an arbitrary defect judgement threshold for an arbitrary inspection area.

The following explains in detail the circuits that are specific to this embodiment.

Figure 19:
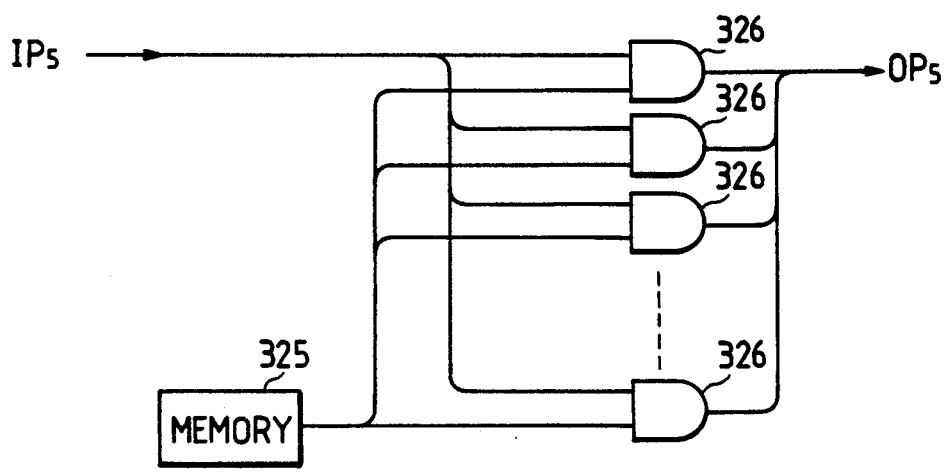
FIG. 19 is a block diagram showing an example of the arrangement of the masking circuit used in the inventive bright/dark field combined illumination, device-to-device comparision method.

FIG. 19 shows, as an example, the arrangement of the masking circuit 308. The masking circuit 209 shown in FIG. 12 deals with image data, whereas the circuit of FIG. 19 deals with multiple tone image data and therefore all bits need to be masked.

Figure 20:
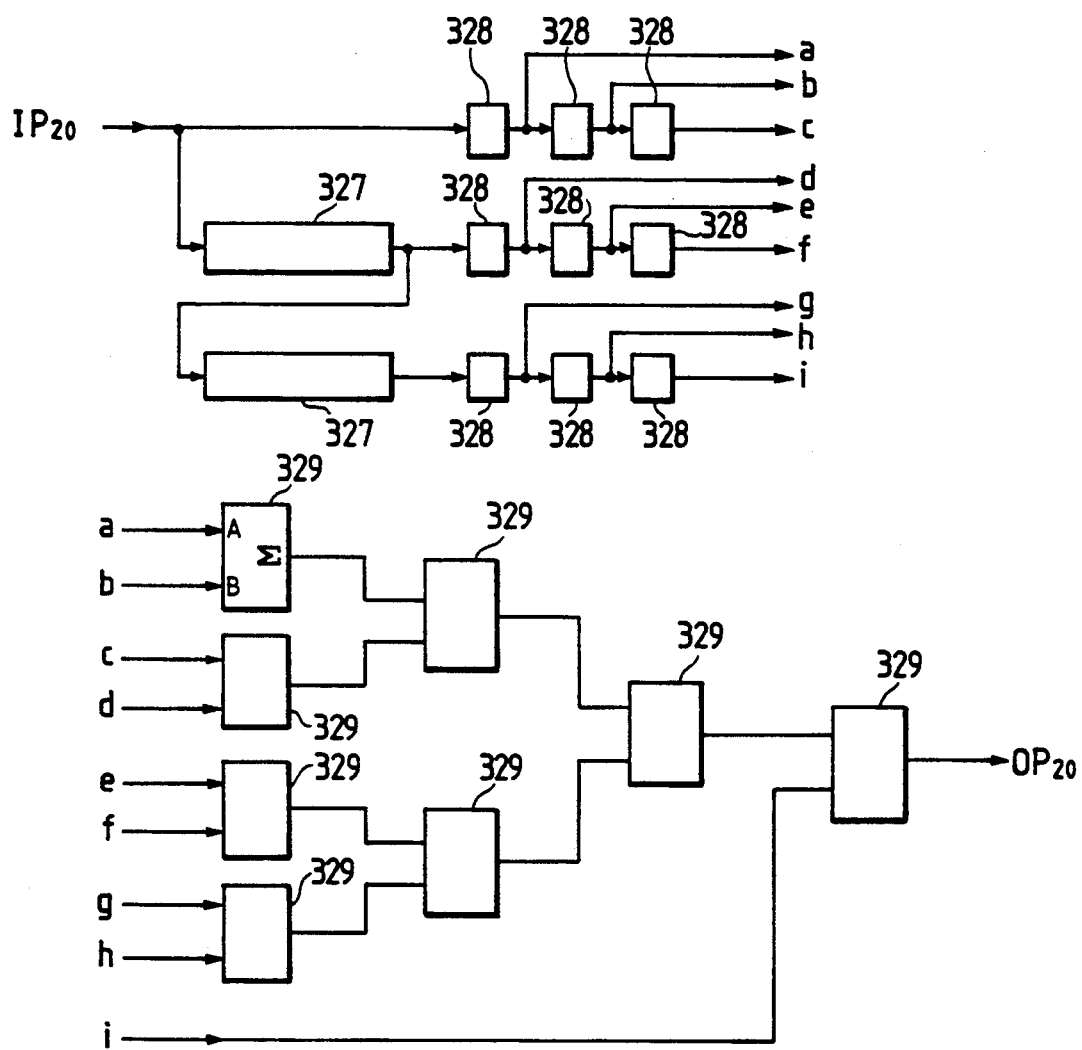
FIG. 20 is a block diagram of an example of the 3-by-3 pixels integration circuit.

FIG. 20 shows, as an example, the arrangement of the 3-by-3 pixels integration circuit 309. Partial image data of 3-by-3 pixels is sliced out of the input image data by means of line memories 327 and latch circuits 328, and the nine output pixel values are summed by summing circuits 329. This process is equivalent to the average filtering process of 3-by-3 pixels, and accordingly inconsistent components which are left unremoved by the masking circuit 308 can be reduced.

Figure 21:
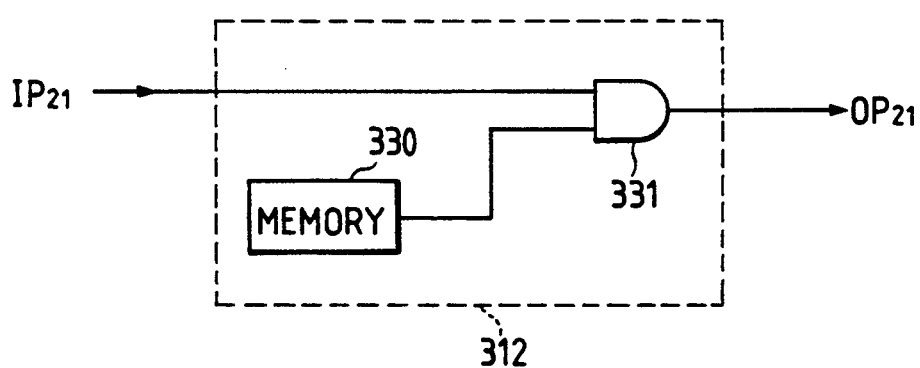
FIG. 21 is a block diagram of an example of the area discrimination circuit.

FIG. 21 shows, as an example, the arrangement of the area discrimination circuit 312. A memory 330 stores image data, with "1" being filled to the area to which the threshold set in the rear-stage size measuring circuit 313 is applied and with "0" being filled to remaining areas. The memory 330 is read out in synchronism with the entry of input image data. Through the logical AND operation for the input image data and the counterpart read out of the memory 330, portions other than the threshold application area are all filled with "0" (absence of defect).

As described above, the inventive bright/dark field combined illumination, device-to-device comparision method is capable of judging defects stably without being affected by bright spots on the element pattern caused by the dark field illumination, following the high-contrast detection of opaque foreign particles existing in the protection layer over an element and etching remnants in the protection layer in the unpatterned area. It is also capable of inspecting a wafer at an arbitrary threshold of defect judgement for an arbitrary test area.

Figure 22A:
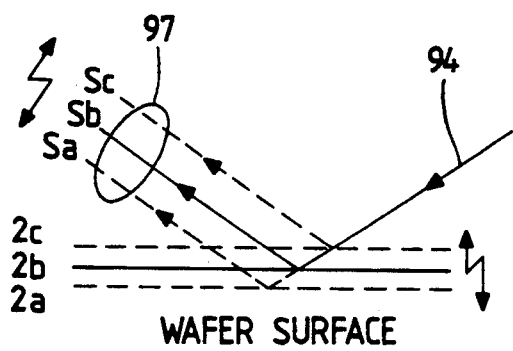
FIGS. 22a to 22c are diagrams showing the principle of the inventive automatic focusing method.
Figure 22B:
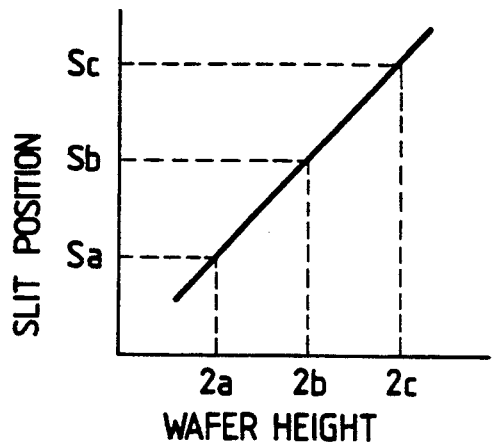
Figure 22C:
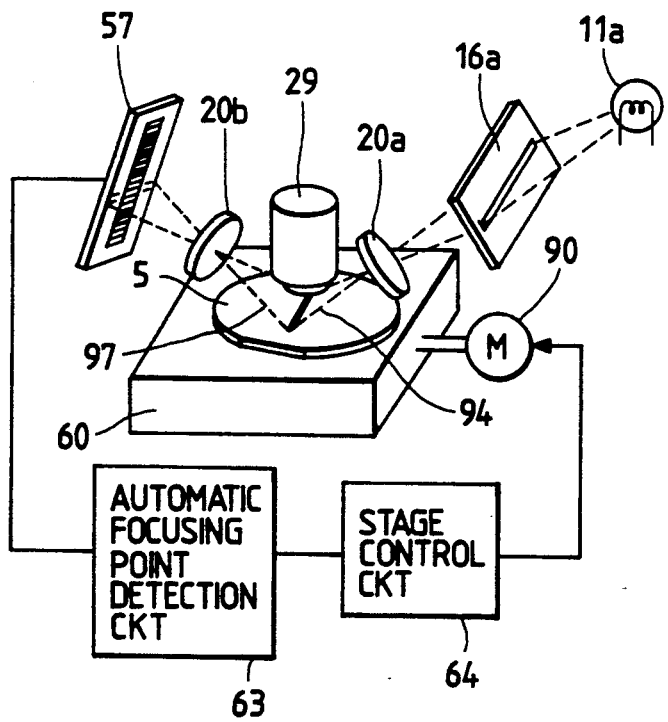

In the inspection methods described above, the wafer under test needs to have its protection layer surface maintained at a constant distance from the illumination system and detection system, and therefore automatic focusing is indispensable. FIGS. 22a-22c show the principle of automatic focusing based on this invention.

As shown in FIGS. 22a and 22b, when the wafer which is illuminated obliquely by a slit light moves vertically to vary its height as shown by 2a, 2b and 2c, the light path of the slit light reflected on the wafer surface is shifted as shown by Sa, Sb and Sc. Accordingly, the height of the wafer surface can be detected through the detection of the position of the reflected slit light. The slit light 97 reflected on the protection layer surface of the wafer 5 is focused on a linear sensor 57 which is installed to have its self scanning direction set perpendicular to the light path of reflected slit light, as shown in FIG. 22c. An automatic focal position detection circuit 63 operates to detect the slit position, i.e., the height of wafer surface, from the image signal produced by the linear sensor 57. A stage control circuit 64 calculates the direction of deviation of the focal position based on the detected height of wafer surface, and drives a motor 90 to move a Z stage 60 vertically.

Figure 23A:
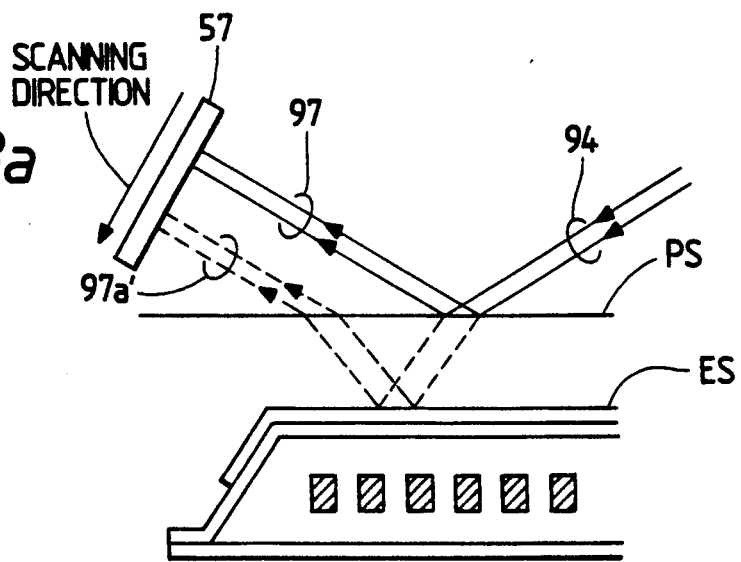
FIGS. 23a and 23b are diagrams explaining the inventive automatic focusing method.

The linear sensor 57 has the self scanning direction as shown in FIG. 23a so that it readily detects the position of the reflected light 97 from the protection layer surface without being disturbed by an unwanted reflection light 97a' from the element surface underneath the protection layer. The linear sensor 57 performs self scanning so that on the detected signal waveform 91 of the linear sensor 57 shown in FIG. 23b, a signal component derived from the light reflected on the protection layer surface PS appears first, and next a signal component derived from the light reflected on the element surface ES under the protection layer appears. The output image signal 91 the linear sensor 57 is converted into a binarization signal 93 at a threshold 92, and the first rising position on the waveform is determined to be the slit position (indicated by coordinate u of the linear sensor), and thereafter the position of reflection of the slit illumination light 94 on the protection layer surface can readily by detected.

Next, the visual inspection apparatus based on the present invention will be described.

Figure 24:
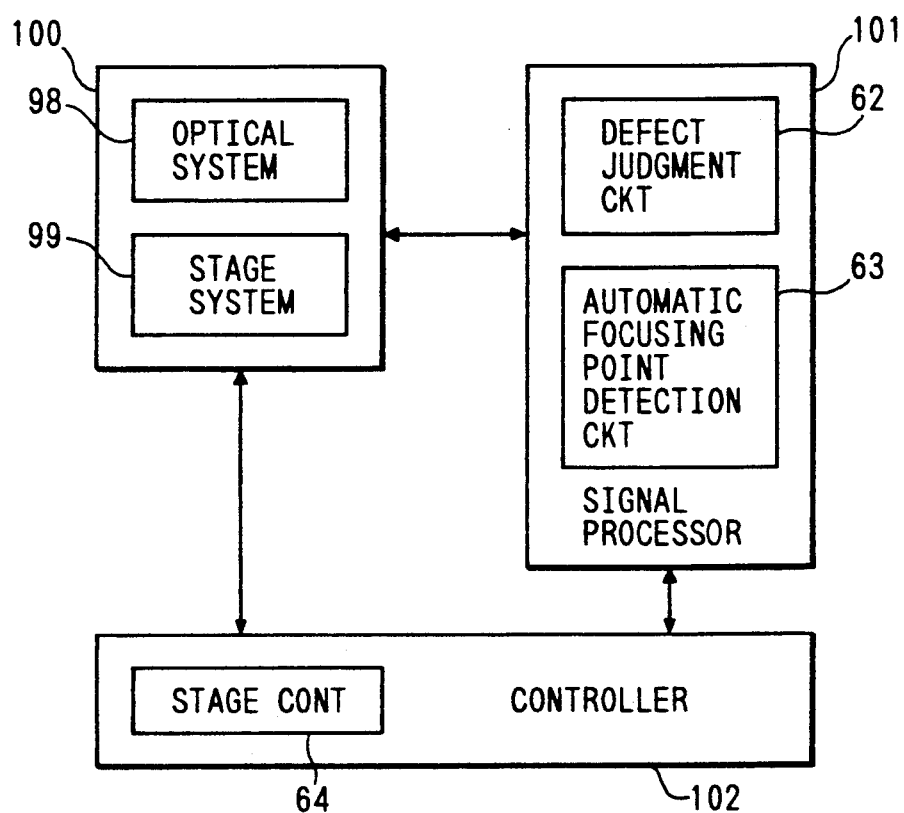
FIGS. 24 and 25 are diagrams showing the defect inspection apparatus based on an embodiment the present invention.

FIG. 24 is a functional block diagram of the visual inspection apparatus based on an embodiment of the present invention. The apparatus consists of a main unit 100, a signal processor 101 and a controller 102. The main unit 100 includes an optical system 98 for illuminating and imaging a wafer and a stage system 99 for moving the wafer relative to the optical system 98. The signal processor 101 includes a defect judgement circuit 62 which processes the image produced by the optical system 98, and an automatic focal position detecting circuit 63. The controller 102 controls the overall system.

The optical system 98 shown in FIG. 24 is broken into three parts, that are a slit light illumination system 70, a detection system 71 and an automatic focusing system 72.

Figure 25:
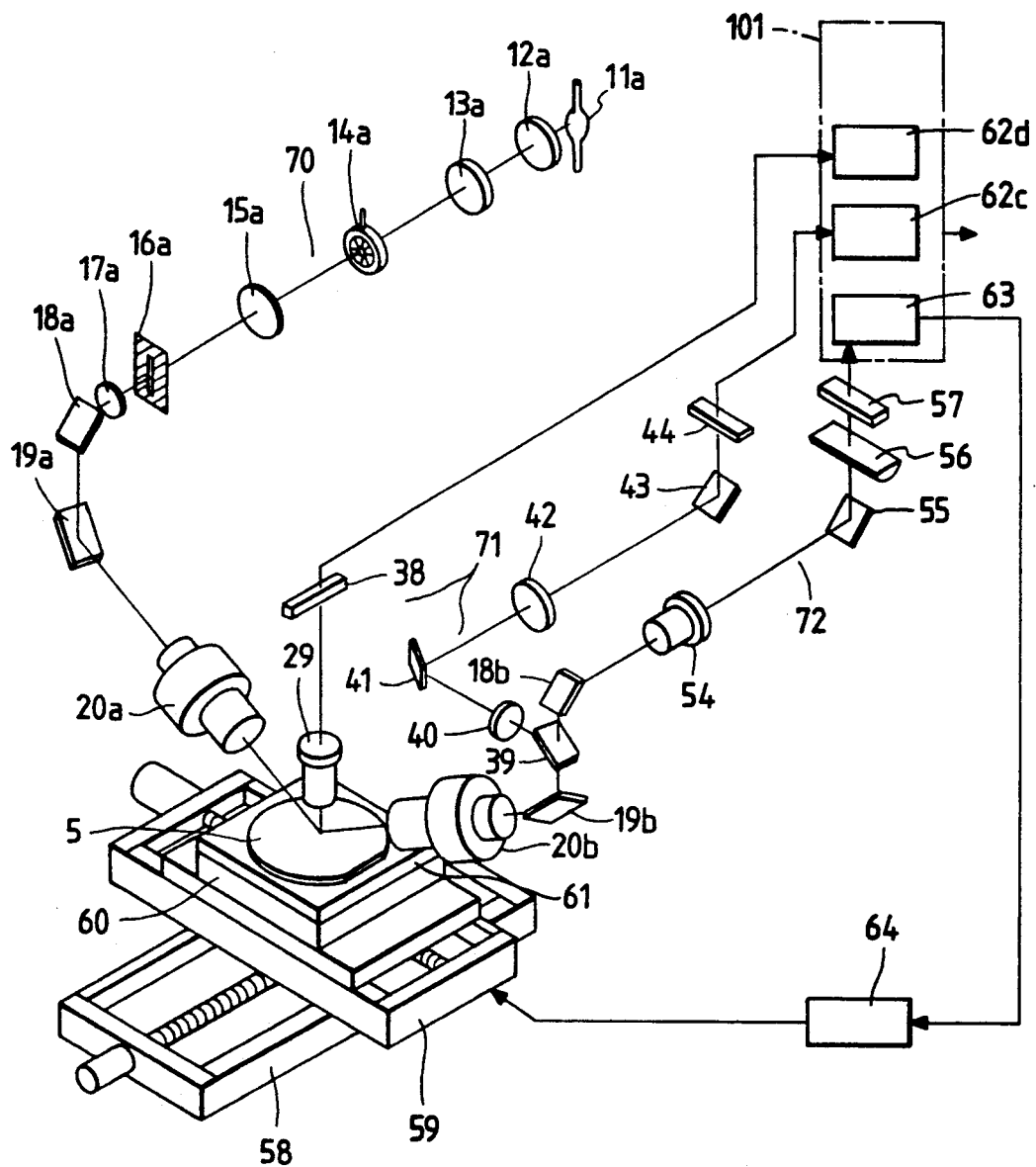

The slit light illumination system 70 shown in FIG. 25 is made up of a light source 11a, collector lens 12a, lens 13a, aperture diaphragm 14a, lens 15a, slit plate 16a, lens 17a, mirrors 18a and 19a, and objective lens 20a.

Slit illumination for the wafer is conducted by projecting a light beam through the slit plate 16a to the wafer.

The detection system shown in FIG. 25 is made up of a scattered light detection system and a reflected light detection system. The scattered light detection system is designed to focus an area 84 shown in FIG. 25 on the linear sensor 38 by means of an objective lens 29. The reflected light detection system is designed to detect a slit light reflected on the protection layer surface of the wafer 5 by means of a linear sensor 44 through an objective lens 20b, mirror 19b, half mirror 39, field lens 40, mirror 41, relay lens 42, and mirror 43. This system clarifies defects of wafers as described previously, and the output signals of the linear sensors 38 and 44 are processed by signal processing circuits 62d and 62c thereby to detect the defects.

Figure 26:
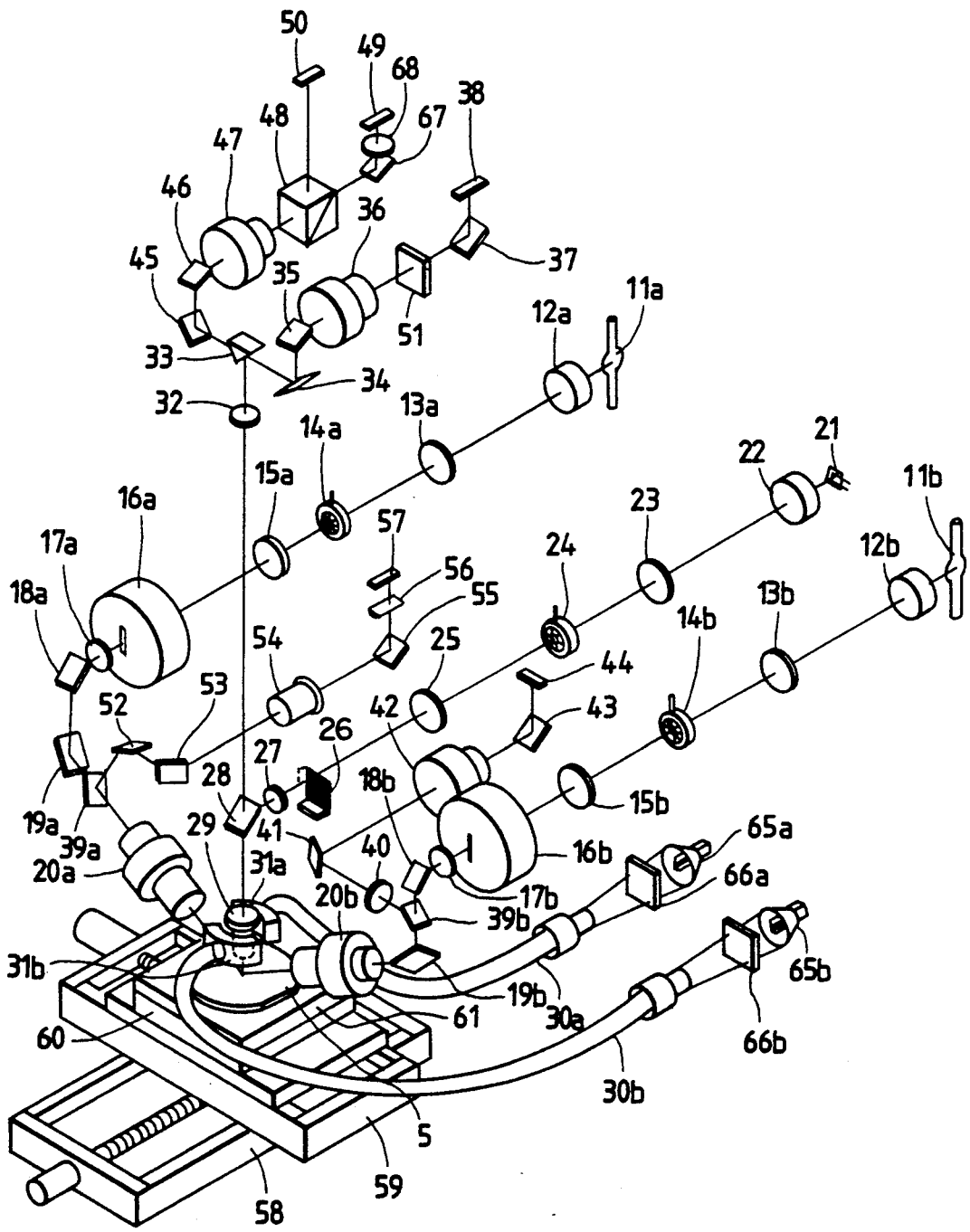
FIG. 26 is a diagram showing the structure of the optical system of the defect inspection apparatus based on an embodiment of the present invention.

FIGS. 25 and 26 show the principal arrangement of the optical system 98 and stage system 99 in the main unit 100 based on an embodiment of this invention. The wafer 5 is placed on a sample stage made up of an X stage 58, Y stage 59, Z stage 60 and θ stage 61, and the wafer is scanned through the movement of the stages 58-61 so that all elements formed on the wafer 5 are imaged for the inspection.

The optical system 98 of FIG. 24 is broken into an illumination system 70, a detection system 71, and an automatic focusing system 72, as shown in FIGS. 25 and 26. The illumination system shown in FIG. 26 made up of the light source 11a, collector lens 12a, lens 13a, aperture diaphragm 14a, lens 15a, slit plate 16a, lens 17a, mirrors 18a and 19a, half mirror 39a, and objective lens 20a will be called a slit light illumination system A. Similarly, a slit light illumination system B is made up of a light source 11b, collector lens 12b, lens 13b, aperture diaphragm 14b, lens 15b, slit plate 16b, lens 17b, mirrors 18b and 19b, half mirror 39b, and objective lens 20b. Slit illumination for the wafer is conducted by projecting light beams through the slit plates 16a and 16b to the wafer.

In this embodiment, the wafer is illuminated in two opposing directions simultaneously so that beams of slit light are incident to the protection layer surface at the same position, whereby the scattered light from a foreign particle in the protection layer is reinforced.

A bright field illumination system is made up of a light source 21, collector lens 22, lens 23, aperture diaphragm 24, lens 25, slit plate 26, lens 27, half mirror 28, and objective lens 29, and it performs Koehler illumination. A dark field illumination system is made up of light sources 65a and 65b, wavelength limiting filters 66a and 66b, glass fiber cables 30a and 30b, and ring illuminators 31a and 31b disposed along a circle at, the end of the glass fiber cables 30a and 30b. The two fan-shaped ring illuminators confronting each other are used, instead of a continuous circular one, thereby to prevent the illumination light beams from the slit illumination systems from being interrupted by the ring illuminator.

The detection system consists of a scattered light detection system, a reflected light detection system, a bright field illumination light detection system, and a bright/dark field combined illumination light detection system. The scattered light detection system is made up of an objective lens 29, half mirror 28, field lens 32, splitting triangular mirror 33, mirrors 34 and 35, relay lens 36, mirror 37, and linear sensor 38, and it focuses the image of the area shown in FIG. 6 on the linear sensor 38. The reflected light detection system operates to detect the slit light produced by the slit illumination system A and reflected on the protection layer surface of the wafer 5 with the linear sensor 44 through the objective lens 20b, mirror 19b, half mirror 39b, field lens 40, mirror 41, relay lens 42 and mirror 43. The bright field illumination light detection system operates to detect the light which is split by the triangular mirror 33 with a linear sensor 50 through mirrors 45 and 46, relay lens 47 and dichroic prism 48. The bright/dark field combined illumination light detection system operates to detect the light which is split by the dichroic prism 48 with a linear sensor 49 through a mirror 67 and magnification correction lens 68.

Figure 27A:
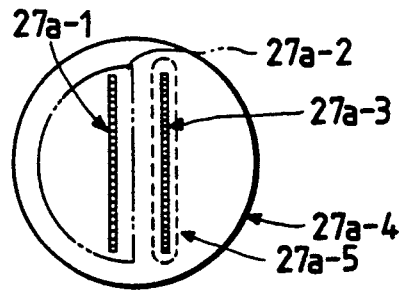
FIGS. 27a to 27c are diagrams explaining the illumination method and device of the inventive defect inspection apparatus.
Figure 27B:
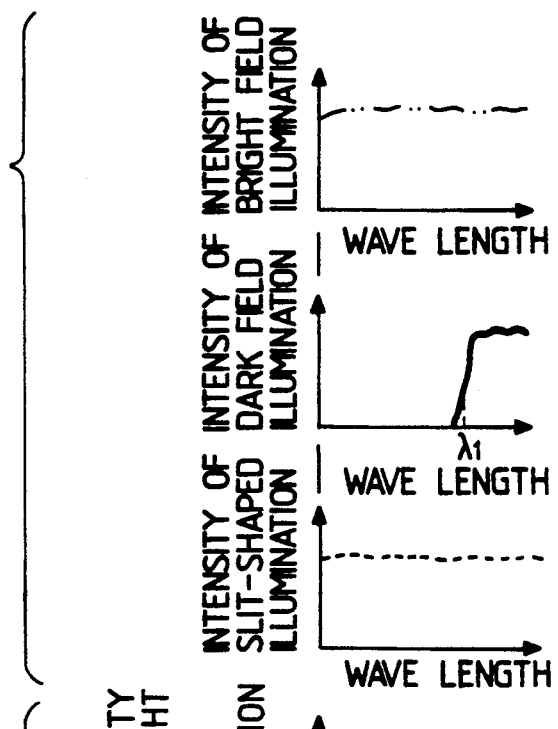
Figure 27C:
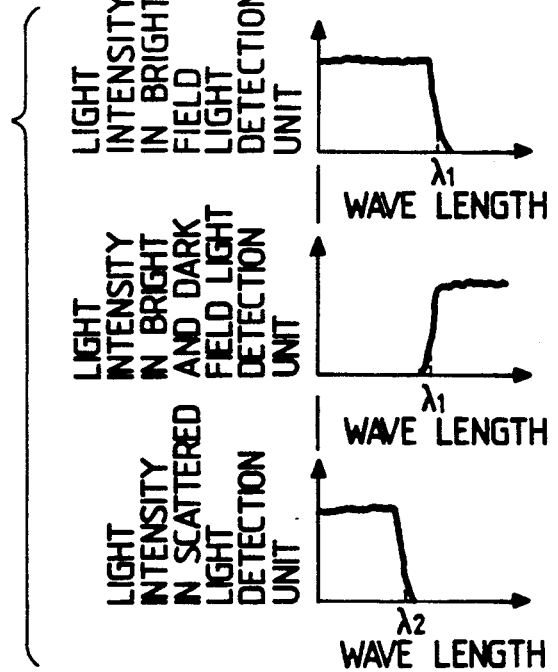

For the simultaneous detection of an image by the three detection systems through the objective lens 29, the illumination systems have their light wavelengths and ranges of illumination limited, and the detection systems have their sensitive light wavelengths limited as shown in FIGS. 27a-27c. In FIG. 27a, indicated by 27a-1 is the detecting position of the bright field light and bright/dark field combined light, 27a-2 is the area of bright field illumination, 27a-3 is the detecting position of the slit scanning light, 27a-4 is the area of bright illumination, and 27a-5 is the area of dark field illumination. The dark field illumination light is confined to wavelengths of $\lambda_1$ or above by means of the wavelength limiting filters 65a and 65b. The bright field illumination light is not confined in its wavelength, but it is limited in its illumination range by means of the slit plate 26. The detected light beams from the objective lens 29 are separated by the splitting triangular mirror 33 for the detecting positions of the scattered light detection system, bright field light detection system and bright/dark field combined light detection system, so that the light with wavelengths of $\lambda_2$ or less is detected by the scattered light detection system through the wavelength limiting filter 51, the light with wavelengths of $\lambda_1$ or above is detected by the bright/dark field combined light detection system through the dichroic prism 48, and the light with wavelengths of $\lambda_1$ or less is detected by the bright field light detection system. Consequently, the three detection systems can operate for image detection simultaneously without interfering with each other.

The automatic focusing system focuses the slit light, which is produced by the slit light illumination system B and reflected on the protection layer surface of the wafer 5, on the linear sensor 57 through the objective lens 20a, half mirror 39a, mirrors 52 and 53, objective lens 54, mirror 55, and cylindrical lens 56. The cylindrical lens 56 is to compress the slit light in its longitudinal direction with the intention of retaining the automatic focusing function against the fading of the slit light due to a small void or the like on the wafer.

Figure 23B:
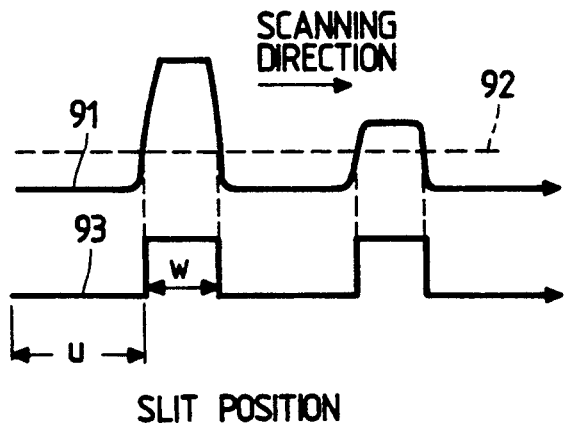

However, even with the provision of the cylindrical lens 56 for the slit light compression, the presence of a large void causes the slit light to diminish greatly in its width, resulting possibly in the failure of correct evaluation of the out-of-focus value based on the rising position of the signal waveform 93 shown in FIG. 23b. The following describes a method of preventing the automatic focusing from malfunctioning even in the presence of a large void.

Figure 28:
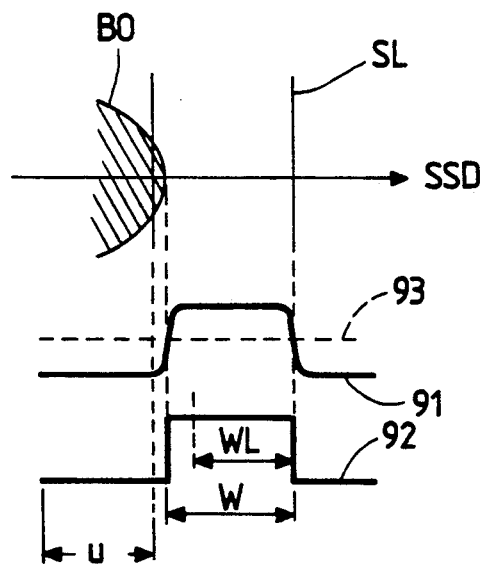
FIG. 28 is a diagram explaining the method of preventing the malfunctioning of the automatic focusing operation.

Referring to FIG. 28, with the lower limit of the slit width being defined as $W_L$, the automatic focal position detection circuit 63 shown in FIGS. 24 and 25 responds to the detection of a too small slit width, indicative of the influence of a void, to block the control signal to the Z stage controller 64 so that the Z stage does not operate. However, if the lower limit $W_L$ is set with a moderate margin so that the usual focusing operation takes place smoothly, an erroneous focusing will occur when the slit SL and the void BO have a spatial relation as shown in FIG. 28. In FIG. 28 indicated by SSD is the sensor's self scanning direction. To cope with this matter, the automatic focal position detecting circuit 63 has a record of information on the slit position to be detected and the slit width, and issues the control signal to the Z stage control circuit 64 so that the Z stage operates only if the slit width is greater than the lower limit value at n-time consecutive detections. The automatic focal position detecting circuit 63 drives the Z stage 60 based on the oldest slit position information $U_{old}$ among the six pieces of information when the wafer moves in the same direction as the scanning direction of the linear sensor 57 (i.e., when the rising position of the slit is shifted backward due to the presence of a void as the wafer moves), or it drives the Z stage 60 based on the latest slit position information $U_{new}$ among the six pieces of information when they have different moving directions (i.e., when the slit width diminishes due to the presence of a void as the wafer moves). In any case, after the Z stage has been moved based on the slit position information, information on the slit width and slit position stored in the automatic focal position detecting circuit 63 becomes meaningless, and it is cleared. In consequence, malfunctioning of automatic focusing caused by a void can be prevented, and at the same time the focusing error can be minimized.

Figure 29:
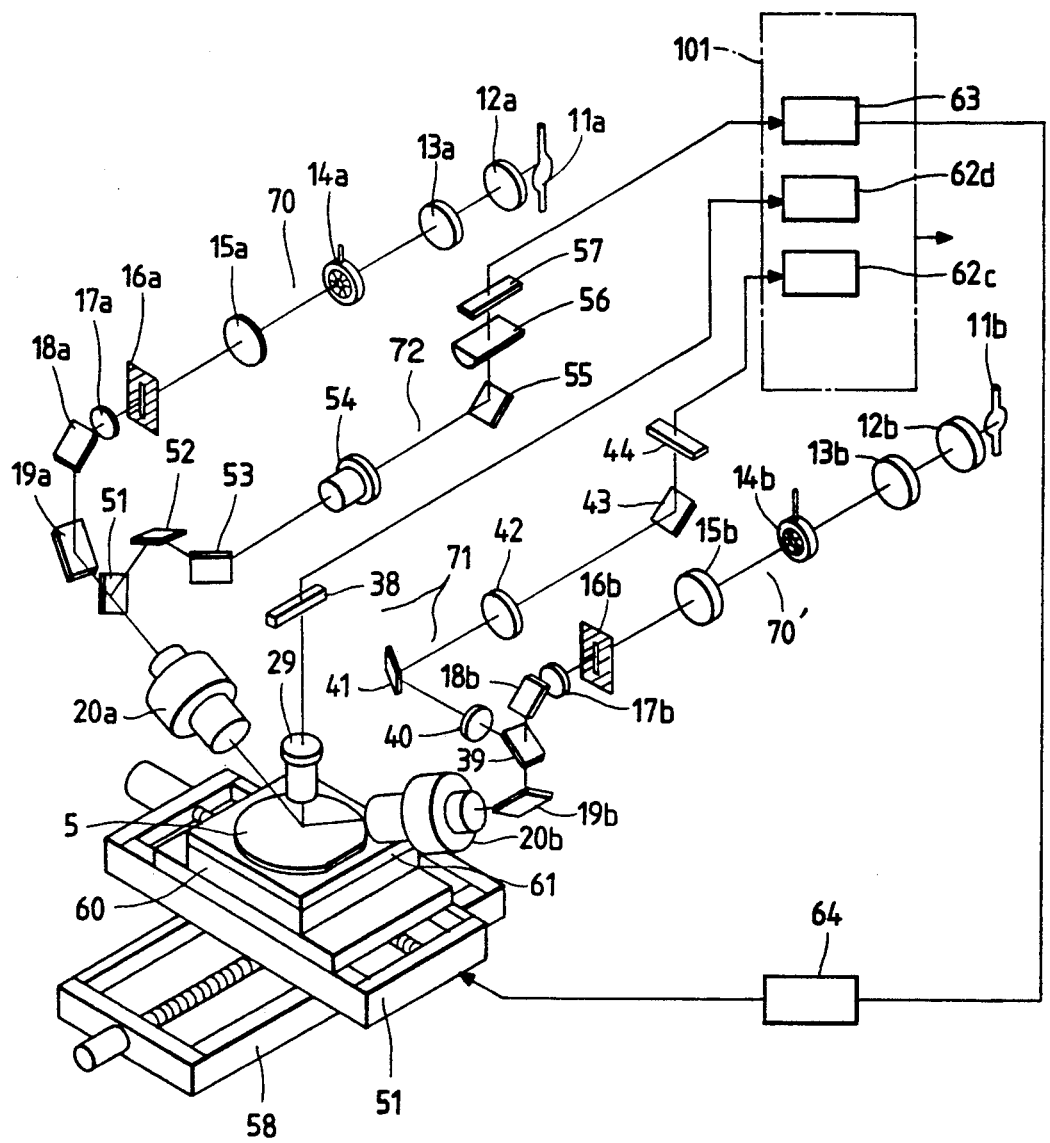
FIG. 29 is a diagram showing the optical systems based on other embodiments of the inventive visual inspection apparatus.

FIG. 29 shows the principal arrangement of the optical system of the visual inspection apparatus based on still another embodiment of this invention. The apparatus includes two confronting slit illumination systems (70 and 70'). Two illumination light beams 70 and 70' are incident to the protection layer surface at the same position so that the scattered light from a foreign particle 6 in the protection layer has an increased intensity for implementing more reliable defect detection. In the reflected light detection system, the slit illumination light projected by the slit light illumination system 70 (including the slit plate 16a) and reflected on the wafer 5 is detected with the linear sensor 44, and a defect is detected with a defect judgement circuit 62c. In the automatic focusing system 72, the reflected light of the slit illumination light from the slit illumination system 70' (including the slit plate 16b) is detected with a linear sensor 57 through the objective lens 20a, half mirror 51, mirrors 52 and 53, objective lens 54, mirror 55, and cylindrical lens 56, and the focal point is detected with the automatic focal position detecting circuit 63.

Although the foregoing embodiments are cases of using slit light illuminations for the scattered light detection and reflected light detection, the visual inspection method of the present invention does not restrict the width of slit. Namely, an applicable illumination light may be such that, in FIG. 7, the slit light may have a very large width D (between 94a and 94b) so that the entire portion of the light above 94a (on the side of 94b) is incident to the object.

The four defect detection methods described in the embodiments can by carried out concurrently as shown in the embodiments of optical systems, and various kinds of defects can surely be detected in a single inspecting operation.

According to the present invention, it is possible to detect reliably a defect of an element coated with a transparent protection layer, such as a thin-film magnetic head used in a magnetic disk unit of a large computer system, existing inside of or on the surface of the protection layer, without being affected by the shape and surface characteristics of the element. In consequence, the conventional visual inspection which relies on the human eye can be automated, and the product is enhanced in reliability and lowered in manufacturing cost significantly.

What is claimed is:

1. A method of inspecting an object, the object including an element coated with a transparent protection layer, to detect a defect within or on the surface of the transparent protection layer, said method comprising:
   illuminating the surface of the object obliquely with a slit-formed illumination light;
   automatically focusing the illumination light on the surface of the transparent protection layer;
   condensing light reflected obliquely from the transparent protection layer;
   converting the condensed reflected light into a first image signal;
   detecting waveforms in the first image signal less than a first threshold level to provide a first defect signal indicative of a void in the surface of the transparent protection layer;
   detecting waveforms in the first image signal greater than a second threshold level to provide a second defect signal indicative of an etching remnant on the surface of the transparent protection layer;
   condensing light scattered from the transparent protection layer in a direction substantially normal to the surface of the transparent protection layer;
   converting the condensed scattered light into a second image signal; and
   detecting waveforms in the second image signal greater than a third threshold level to provide a third defect signal indicative of a transparent foreign body in the transparent protective layer.

2. An apparatus for inspecting an object, the object including an element coated with a transparent protection layer, to detect a defect within or on the surface of the transparent protection layer, said apparatus comprising:
   means for illuminating the surface of the object obliquely with a slit-formed illumination light;
   means for automatically focusing the illumination light on the surface of the transparent protection layer;
   means for condensing light reflected obliquely from the transparent protection layer;
   means for converting the condensed reflected light into a first image signal;
   means for detecting waveforms in the first image signal less than a first threshold level to provide a first defect signal indicative of a void in the surface of the transparent protection layer;
   means for detecting waveforms in the first image signal greater than a second threshold level to provide a second defect signal indicative of an etching remnant on the surface of the transparent protection layer;
   means for condensing light scattered from the transparent protection layer in a direction substantially normal to the surface of the transparent protection layer;
   means for converting the condensed scattered light into a second image signal; and
   means for detecting waveforms in the second image signal greater than a third threshold level to provide a third defect signal indicative of a transparent foreign body in the transparent protective layer.

3. A defect inspection apparatus according to claim 2, wherein said illuminating means comprises at least one pair of symmetrically disposed illumination devices.

4. A defect inspection apparatus according to claim 2 in which said automatically focusing means includes position information detecting means for detecting the position of the slit-formed light projected on the surface of the transparent protection layer.

5. A method of inspecting an object, the object including an element coated with a transparent protection layer, to detect defects within or on the surface of the transparent protection layer, said method comprising:
   illuminating the object obliquely with an illumination light;
   converting light reflected obliquely from the surface of the transparent protection layer into a first image signal;
   detecting waveforms in the first image signal less than a first threshold level to provide a first defect signal indicative of a void in the surface of the transparent protection layer;
   detecting waveforms in the first image signal greater than a second threshold level to provide a second defect signal indicative of an etching remnant on the surface of the transparent protection layer;
   converting light scattered from the transparent protection layer in a direction substantially normal to the surface of the transparent protection layer into a second image signal; and
   detecting waveforms in the second image signal greater than a third threshold level to provide a third effect signal indicative of a foreign particle within the transparent protection layer.

6. An apparatus for inspecting an object, the object including an element coated with a transparent protection layer, to detect defects within or on the surface of the transparent protection layer, said apparatus comprising:
   means for illuminating the object obliquely with an illumination light;
   means for converting light reflected obliquely from the surface of the transparent protection layer into a first image signal;
   means for detecting waveforms in the first image signal less than a first threshold level to provide a first defect signal indicative of a void in the surface of the transparent protection layer;
   means for detecting waveforms in the first image signal greater than a second threshold level to provide a second defect signal indicative of an etching remnant on the surface of the transparent protection layer;
   means for converting light scattered from the transparent protection layer in a direction substantially normal to the surface of the transparent protection layer into a second image signal; and
   means for detecting waveforms in the second image signal greater than a third threshold level to provide a third defect signal indicative of a foreign particle within the transparent protection layer.

* * * * *